(12) United States Patent
Venkataraman et al.

(10) Patent No.: US 7,112,697 B1
(45) Date of Patent: Sep. 26, 2006

(54) METHODS FOR FORMATION OF ARYL-SULFUR AND ARYL-SELENIUM COMPOUNDS USING COPPER(I) CATALYSTS

(75) Inventors: Dhandapani Venkataraman, Hadley, MA (US); Craig G. Bates, South Hadley, MA (US); Rattan K. Gujadhur, Plainsboro, NJ (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 10/889,311

(22) Filed: Jul. 12, 2004

Related U.S. Application Data

(60) Provisional application No. 60/527,460, filed on Dec. 5, 2003, provisional application No. 60/486,538, filed on Jul. 11, 2003.

(51) Int. Cl.
*C07C 391/02* (2006.01)
*B01J 31/00* (2006.01)

(52) U.S. Cl. .................. 568/68; 568/77; 562/899; 502/165; 252/183.13

(58) Field of Classification Search .............. 568/68, 568/77; 562/899; 502/165; 252/183.13
See application file for complete search history.

(56) References Cited

U.S. PATENT DOCUMENTS

| 6,395,939 B1 * | 5/2002 | Marcoux et al. ............ 568/635 |
| 6,762,329 B1 * | 7/2004 | Marcoux et al. ............ 568/635 |
| 2003/0088128 A1 * | 5/2003 | Marcoux et al. ............. 568/17 |

OTHER PUBLICATIONS

Alexey V. Kalinin, Justin F. Bower, Peter Riebel, and Victor Snieckus, "The Directed Ortrho Metalation—Ullmann Connection. A New Cu(I)-Catalyzed Variant for the Synthesis of Substituted Diaryl Ethers," *J. Org. Chem.*, 1999 American Chemical Society, p. 2986-87, vol. 64, published on Web Apr. 15, 1999.

Claudio Palomo, Mikel Oiarbide, Rosa López, and Enrique Gómez-Bengoa, "Phosphazene bases for the preparation of biaryl thioathers from aryl iodides and arenthoils," *Tetrahedron Letters*, 2000 Elseview Science, Ltd., p. 1283-86, vol. 41.

Rattan K. Gujadhur, Craig G. Bates, and D. Venkataraman, "Formation of Aryl-Nitrogen, Aryl-Oxygen, and Aryl-Carbon Bonds Using Well-Defined Copper(I)-Based Catalysts," *Organic Letters*, 2001 American Chemical Society, p. 4315-17, vol. 3, No. 26, published on Web Nov. 22, 2001.

Craig G. Bates, Rattan K. Gujadhur, and D. Venkataraman, "A General Method for the Formation of Aryl-Sulfur Bonds Using Copper(I) Catalysts," *Organic Letters*, 2002 American Chemical Society, p. 2803-08, vol. 4, No. 16, published on Web Jul. 12, 2002.

Fuk Yee Kwong and Stephen L. Buchwald, "A General, Efficient, and Inexpensive Catalyst System for the Coupling of Aryl Iodides and Thiols," *Organic Letters*, 2002 American Chemical Society, p. 3517-20, vol. 4, No. 20, published on Web Sep. 11, 2002.

Rattan K. Gujadhur and D. Venkataraman, "A general method for the formation of diaryl seinides using copper(I) catalysts," *Tetrahedron Letters*, 2002 Elseview Science Ltd., p. 81-84, vol. 44.

* cited by examiner

*Primary Examiner*—Porfirio Nazario-Gonzalez
(74) *Attorney, Agent, or Firm*—Reinhart Boerner Van Deuren s.c.

(57) ABSTRACT

A mild, palladium-free synthetic protocol for the cross-coupling reaction of vinyl or aryl iodides and thiols or selenols using, in certain embodiments, 10 mol % CuI and 10 mol % neocuproine, with NaOt-Bu as the base, in toluene at 110 ° C. A variety of vinyl/aryl sulfides and vinyl/aryl selenides can be synthesized in excellent yields from readily available iodides and thiols or selenols.

20 Claims, 3 Drawing Sheets

METHODS FOR FORMATION OF ARYL-SULFUR AND ARYL-SELENIUM COMPOUNDS USING COPPER(I) CATALYSTS

This application claims priority benefit from U.S. provisional application No. 60/486,538 filed Jul. 11, 2003 and U.S. provisional application No. 60/527,460 filed Dec. 5, 2003, each of which is incorporated herein by reference in its entirety.

The United States government has certain rights to this invention pursuant to Grant No. CHE-0134287 from the National Science Foundation to the University of Massachusetts.

BACKGROUND OF INVENTION

Methods for the formation of aryl-sulfur bonds are indispensable tools in synthetic chemistry. Their importance stems from the prevalence of aryl-sulfur bonds in many molecules that are of biological, pharmaceutical and materials interest. Similarly, diaryl selenides have attracted considerable interest because of their potential as anticancer and antioxidant agents. They are also key intermediates in the synthesis of a plethora of biologically and pharmaceutically important selenium compounds such as selenonium salts, selenoxides, selenimines, and selenide dihalides. In recognition of their importance, various synthetic methods for the formation of diaryl selenides have been reported in the literature.

Traditional methods for the synthesis of aryl-sulfur bonds often require harsh reaction conditions. For example, coupling of copper thiolates with aryl halides requires polar solvents such as HMPA and temperatures around 200° C. Reduction of aryl sulfones or aryl sulfoxides requires strong reducing agents such as DIBAL-H or $LiAlH_4$. Likewise, earlier selenide preparatory methods often required photochemical or harsh reaction conditions such as the use of polar, toxic solvents such as HMPA and high reaction temperatures. Other reported protocols include the reaction of aryl halide and benzeneselenate anion in liquid ammonia under UV light and the reaction of sodium selenide with arenediazonium salts.

In 1980, Migita and co-workers first reported the cross-coupling reaction of aryl halides and thiols with $Pd(PPh_3)_4$ as the catalyst and NaOt-Bu as the base in polar solvents such as refluxing ethanol or DMSO at 90° C. Thereafter, however, few reports have appeared in the literature for the formation of aryl-sulfur bonds using transition metal catalysts, and then only for Pd(0) or Ni(0)—in sharp contrast to the volume of literature that exists for the formation of aryl-nitrogen and aryl-oxygen bonds. In 1996, following Hartwig's mechanistic studies on the reductive elimination of palladium(II) arylthiolate complexes with chelating phosphines, Zheng and co-workers reported the first general palladium-based protocol for the synthesis of aryl sulfides from aryl triflates. More recently, in 2001, Schopfer and Schlapbach reported a general palladium-catalyzed method for the synthesis of aryl sulfides from aryl iodides, in toluene, using DPEPhos as the ligand.

The current state of aryl-selenium chemistry can be viewed from an analogous historical perspective. In recent years, only a handful of reports have appeared in the literature with synthetic protocols for the formation of aryl-selenium bonds that are general, mild and tolerant. In 1985, Cristau and co-workers first showed that aryl selenides can be obtained by a cross-coupling reaction of aryl halides and sodium benzeneselenolate using Ni(II)-based catalysts. In 2000, Millois and Diaz modified and extended Cristau's method to accommodate diaryl diselenide as a starting material instead of sodium benzeneselenolate. Very recently, the groups of Nishiyama and Beletskaya have independently reported protocols for the cross coupling reaction of aryl iodides and $PhSeSnBu_3$ using palladium-based catalysts.

Various concerns in the art, however, continue to prompt development of new catalytic systems. In particular, the price of palladium is prohibitive, having risen by about 900% in recent years. Further, expensive ligands are required for employment of palladium in reactions of interest. As a result, alternate metals and ligand systems have been the subject of increased study. One such approach involves copper-based systems. Traditional copper-mediated reactions suffer from drawbacks such as high reaction temperatures, the use of copper salts in greater than stoichiometric amounts, sensitivity to functional groups on the aryl halide and irreproducibility. Yet, they remain as the reactions of choice in large- and industrial-scale syntheses. As such, in the past five years, there has been a resurgence in interest in developing mild synthetic methods based on copper-based catalysts as an alternative to palladium(0) catalysts for the formation of aryl-carbon and aryl-heteroatom bonds. In this regard, several research groups have reported copper-based methods for the formation of aryl-carbon, aryl-nitrogen and aryl-oxygen bonds. In addition to being simple and mild, these protocols also accommodate substrates that do not otherwise undergo coupling by palladium catalysis. Moreover, from an economic standpoint and in comparison to palladium, copper-based catalysts are quite attractive. However, several concerns remain, as such catalytic systems have shown limited utility—in particular, with respect to the formation of aryl-sulfur and/or aryl-selenium bonds.

SUMMARY OF THE INVENTION

In light of the foregoing, it is an object of the present invention to provide one or more catalysts or catalytic systems for use in aryl-sulfur or aryl-selenium bond formation, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide a copper (I)-based catalyst useful in aryl-sulfur or aryl-selenium bond formation at catalytic and/or less than stoichiometric concentrations.

It is another object of the present invention to provide a catalyst and/or catalytic system for coupling aryl-halides and thiols or selenols using solvents, reagents, and/or reaction media otherwise common to large and industrial-scale synthetic preparations.

It is another object of the present invention to provide a catalyst and/or catalytic system effective in aryl-sulfur or aryl-selenide bond formation, without resort to palladium catalysis, over a wide range of aryl-halide and thiol or selenol starting materials.

It is another object of this invention to extend the methodologies herein to use of other enyl halides, in addition to aryl halides, such as the synthesis of vinyl sulfides from vinyl halides and thiols.

Other objects, features, benefits and advantages of the present invention will be apparent from this summary and its descriptions of various embodiments, and will be readily apparent to those skilled in the art having knowledge of metal-catalyzed bond formation and coupling reactions. Such objects, features, benefits and advantages will be apparent from the above as taken into conjunction with the accompanying examples, tables, data, figures and all reasonable inferences to be drawn therefrom.

Figure 1:
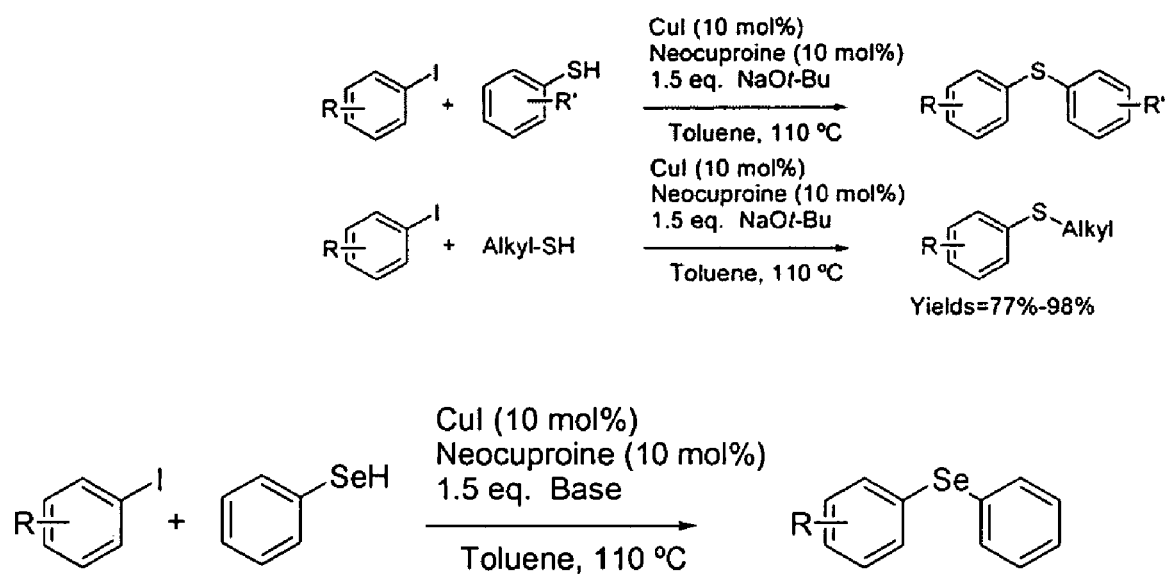
FIG. 1 shows two representative reaction schemes for aryl-sulfur and aryl-selenium bond formation, using Cu(I) halide, ligand and base components in accordance with this invention.
Figure 2:
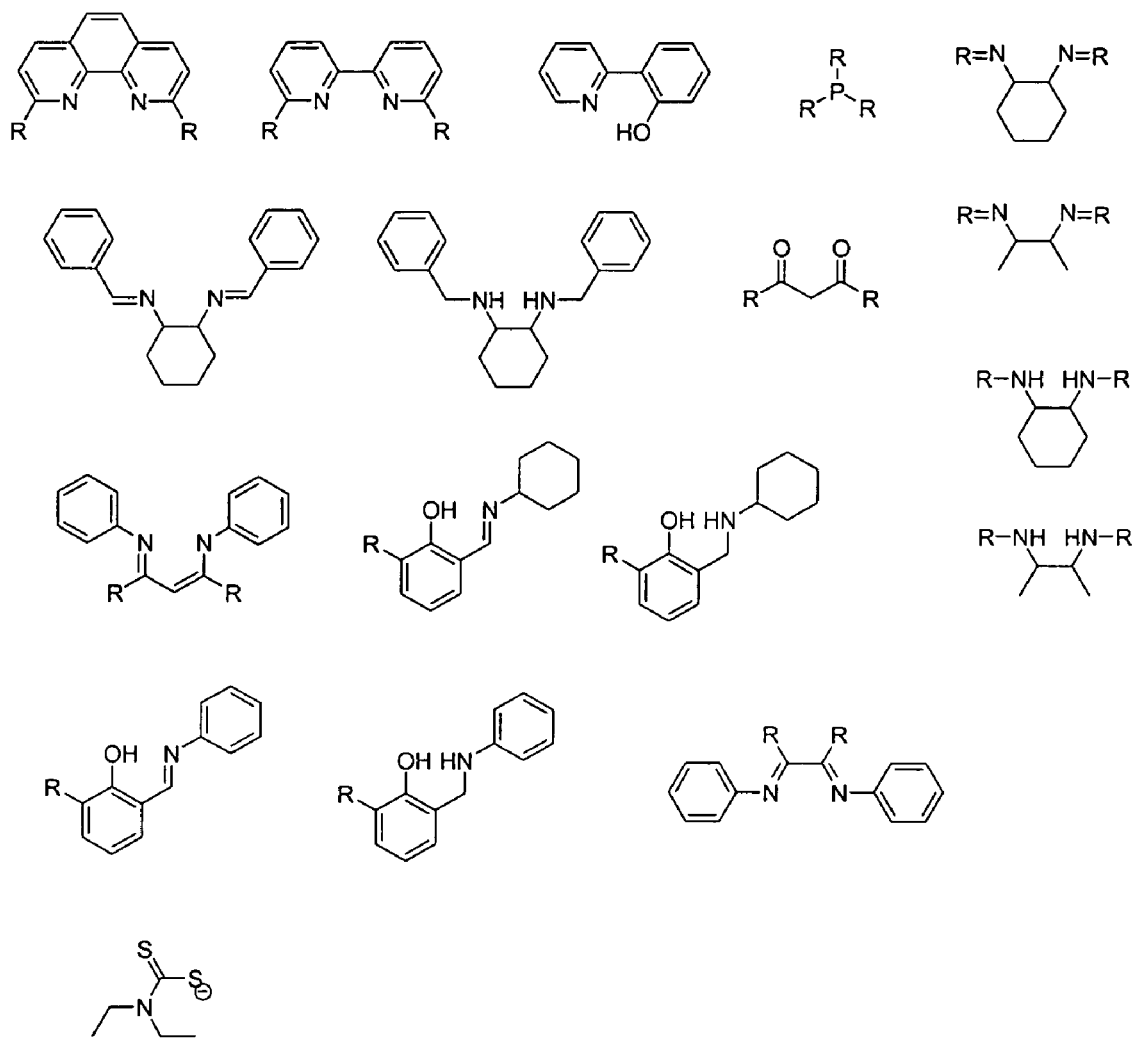
FIG. 2 provides structures of a non-limiting range of ligand components of the type useful in conjunction with the present invention, where R is without limitation independently H, Me, Et, nBu, tBu, iPr, phenyl, aryl or cyclohexyl.
Figure 3A:
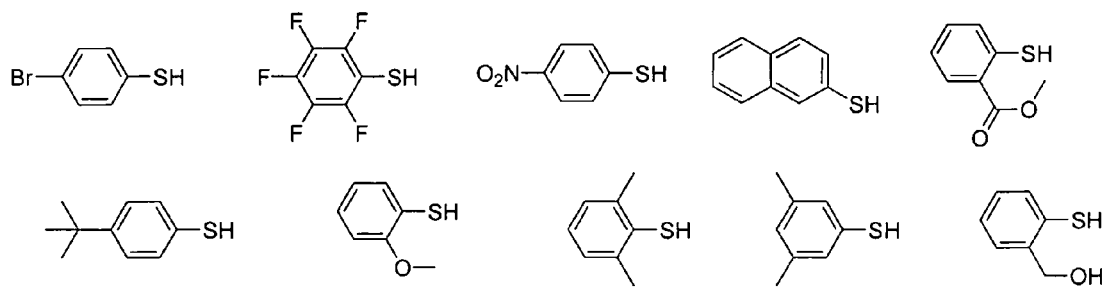
FIGS. 3A–D provide structures of non-limiting thiols and vinyl halides, any combination of which can be used for the synthesis of vinyl sulfides, in accordance with this invention.
Figure 3B:
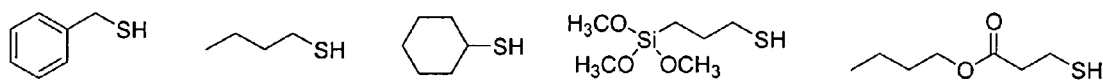
Figure 3C:
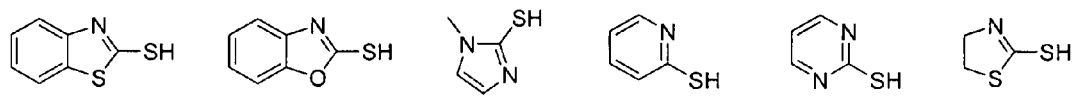
Figure 3D:
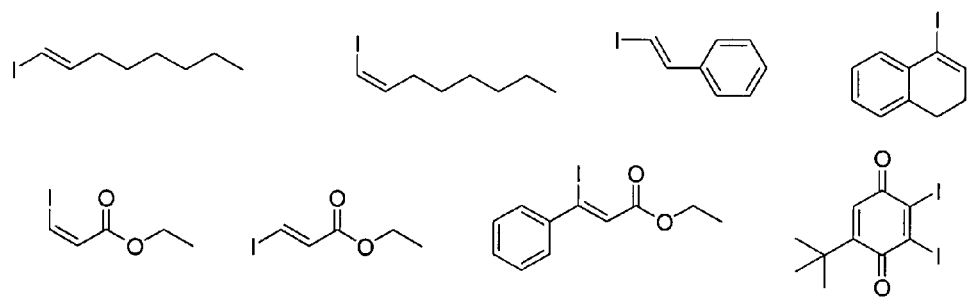

The present invention includes, in part, a method of using a copper (I) metal-ligand compound in aryl-sulfur or aryl-selenium bond formation. Such a method comprises (1) providing a medium comprising either a thiol or a selenol compound and an aryl-halide compound; and (2) contacting such a medium with a copper (I) metal-ligand compound comprising a copper (I) halide and a bi-dentate ligand. (See, FIG. 1 and representative reaction schemes.) Various bi-dentate ligands can be employed herewith, as would be well-known to those skilled in the art made aware of this invention. Reference is made to FIG. 2 and the structures of nonlimiting representative ligand components, either commercially available or as could be obtained via known synthetic procedures or straight-forward modifications thereof. Without limitation, in certain embodiments, ligands such as neocuproine and 1,10-phenanthroline can be used with good effect. Likewise, while certain embodiments of this invention utilize copper iodide, various other copper (I) halides can be used en route to a particular metal-ligand compound. Depending upon choice of reagent or starting material, such a metal-ligand compound can further comprise a triphenylphosphine and/or bromide ligand. Regardless, such a medium can further comprise a base component. In certain embodiments, cesium carbonate or potassium phosphate can be employed. In certain other embodiments, sodium tert-butoxide can be used to provide good yields of the desired coupling reaction product.

As mentioned above, the copper (I) metal-ligand compounds of this invention can be utilized with a range of selenols or thiols and aryl-halide compounds. While certain embodiments of this inventive methodology employ aryl-iodides, various other halide components can be utilized regardless of selenol or thiol identity. As demonstrated below, such aryl-halides can be coupled, via aryl-sulfur or aryl-selenium bond formation, with a range of aryl (e.g., substituted and unsubstituted selenols or thiophenols) heterocyclic (e.g., pyridinyl, benzoxazolinyl, etc.) or alkyl (e.g., $C_1$–about $C_{10}$ substituted and unsubstituted, linear or cyclic) selenols or thiols. The choice of selenol or thiol is limited only by those reagents or materials commercially available or as could be obtained via known synthetic procedures or straight-modifications thereof as would be understood by those skilled in the art. A benefit of the present methodologies is use of a solvent and/or liquid medium comparable to or currently used in preparatory or industrial scale syntheses. While toluene is used effectively, various other solvent or liquid media can be used depending upon choice of reagent or aryl halide/thiol/selenol starting material, required solubility and/or desired reaction parameters.

In part, the present invention can also include a method for coupling aryl-halides and either selenols or thiols. Such a method comprises (1) providing a medium comprising a selenol or thiol compound and an aryl-halide or aryl-iodide compound; and (2) introducing such a medium to another medium comprising a copper (I) metal-ligand compound. Such metal-ligand compounds are as described above with the corresponding copper (I) halide and bi-dentate ligand components, each of which can be present in catalytic concentrations, as compared to either the selenol/thiol or aryl-halide/iodide compound introduced. Such a metal-ligand compound can further comprise one or more additional ligand components depending upon the copper (I) halide utilized (e.g., triphenylphosphine and bromide utilizing tris(triphenylphosphine) copper (I) bromide). Preferably, in the presence of a base, such metal-ligand compounds can be used to couple a range of aryl-iodides with aryl or alkyl selenols/thiols, as discussed more thoroughly above.

Aryl halides represent a group of reactants whereby a halide is pendent to a double-bonded carbon or enyl moiety. Another such enyl moiety is presented by vinyl halides which can also be coupled to either selenols or thiols, in accordance herewith, with a comparable range of Cu(I) metal-ligand compounds and base components.

In light of the preceding, the present invention can also include a system for copper (I) catalyzed aryl-sulfur or aryl-selenium bond formation. Such a system comprises a chelation product of a copper (I) halide with a bi-dentate ligand, and a thiol or selenol compound capable of interacting with such a chelation product en route to reaction with an aryl-halide and subsequent aryl-sulfur or aryl-selenium bond formation. Such reactive interaction is a surprising departure from the prior art. Without restriction any one mechanistic consideration or mode of operation, the results obtained herein are contrary to those predicted in the art under hard-soft/acid-base theory. Soft sulfur or selenium and copper moieties would be expected to provide, respectively, a strong bonding interaction not conducive to further reaction (i.e., typical sulfur poisoning of transition metal catalysts). From another perspective, as hard-soft heteroatom-copper interactions of the prior art lead to corresponding bond formation, neither aryl-sulfur nor aryl-selenium coupling would be expected. However, as apparent from the data and results provided herein, such copper-sulfur and copper-selenium interactions of the present invention proceed with desired aryl-sulfur or aryl-selenium bond formation, contrary to both accepted theory and prior observation.

As outlined above, the present invention demonstrates the utility of copper-based catalysts for the formation of either aryl-selenium or aryl-sulfur bonds through the cross-coupling reaction between aryl iodides and selenols or thiols. In particular, a palladium-free method is provided for the formation of such bonds from aryl iodides using, for example, catalytic amounts of copper iodide and neocuproine (2,9-dimethyl-1,10-phenanthroline).

The efficacy of the present copper(I)-based catalysts was initially observed in the cross-coupling reaction between iodobenzene and thiophenol, in toluene, using Cu(phenanthroline)(PPh$_3$)Br and Cu(neocuproine)(PPh$_3$)Br complexes. With $Cs_2CO_3$ as a base the formation of diphenyl sulfide was observed over 24 h by GC analyses, but overall conversion was less than 50%. Replacing $Cs_2CO_3$ with NaOt-Bu resulted in complete consumption of the starting materials when Cu(neocuproine)(PPh$_3$)Br was used as the catalyst. However, if Cu(phenanthroline)(PPh$_3$)Br was used as the catalyst, GC traces showed the presence of starting materials in trace amounts in the same time period. Trace amounts of starting materials were also observed if KOt-Bu was used as the base. Diphenyl sulfide was formed only in trace amounts if bromobenzene was used indicating that the reaction was selective but not exclusive to iodides.

To further characterize other embodiments of this methodology, Cu-(neocuproine)(PPh$_3$)Br was substituted with 10 mol % CuI, CuI/neocuproine or CuCl/neocuproine as the catalyst. CuI/neocuproine was as effective as Cu(neocuproine)(PPh$_3$)Br. However, only a trace amount of diphenyl sulfide was observed if CuI alone was used as the catalyst. Also, GC traces indicated the presence of starting materials if CuCl/neocuproine was the catalyst. While K$_3$PO$_4$ was as effective as KOtBu, other bases such as triethylamine and K$_2$CO$_3$ were less effective in the coupling of iodobenzene with thiophenol. On the basis of such observations, several representative reaction systems were examined using CuI (10 mol %)/neocuproine (10 mol %) as a catalyst, NaOt-Bu as a base and toluene as a solvent—as a non-exclusive protocol for the formation of aryl-sulfur bonds.

Using this protocol, thiophenol was coupled with electron-rich and electron-poor aryl iodides in excellent yields (Table 1). Furthermore, a variety of readily available thiophenols were coupled with iodobenzene in excellent yields (Table 2). Note that this protocol can also be used to couple sterically hindered thiophenols such as 2,6-dimethylthiophenol with iodobenzene in 95% yield (entry 7, Table 2). Moreover, the methodology can also be extended to couple aryl halides with alkyl thiols (e.g., n-butyl sulfide) in excellent yields (Table 3).

TABLE 1

Reactions of Aryl Iodides with Thiophenol

| Entry | Aryl Iodide | Product | Isolated Yield (%) |
|---|---|---|---|
| 1 | 4-methyl-iodobenzene | 4-methylphenyl phenyl sulfide | 94 |
| 2 | 2-methyl-iodobenzene | 2-methylphenyl phenyl sulfide | 96 |
| 3 | 4-methoxy-iodobenzene | 4-methoxyphenyl phenyl sulfide | 96 |
| 4 | 2-methoxy-iodobenzene | 2-methoxyphenyl phenyl sulfide | 95 |
| 5 | methyl 4-iodobenzoate | methyl 4-(phenylthio)benzoate | 84 |

TABLE 1-continued

Reactions of Aryl Iodides with Thiophenol

R—⟨⟩—I + ⟨⟩—SH  →  [CuI (10 mol %), Neocuproine (10 mol %), 1.5 eq. NaOt-Bu, Toluene, 110° C.]  →  R—⟨⟩—S—⟨⟩

| Entry | Aryl Iodide | Product | Isolated Yield (%) |
|---|---|---|---|
| 6 | methyl 2-iodobenzoate | methyl 2-(phenylthio)benzoate | 81 |
| 7 | 2-iodo-1,3,5-trimethylbenzene | 2-(phenylthio)-1,3,5-trimethylbenzene | 97 |
| 8 | 2-iodophenol | 2-(phenylthio)phenol | 81 |
| 9 | 2-iodothiophene | 2-(phenylthio)thiophene | 91 |

TABLE 2

Reactions of Iodobenzene with Readily Available Thiophenols

⟨⟩—I + ⟨⟩(R)—SH  →  [CuI (10 mol %), Neocuproine (10 mol %), 1.5 eq. NaOt-Bu, Toluene, 110° C.]  →  ⟨⟩—S—⟨⟩—R

| Entry | Thiol | Product | Isolated Yield (%) |
|---|---|---|---|
| 1 | thiophenol | diphenyl sulfide | 98 |
| 2 | 4-methylthiophenol | 4-methyldiphenyl sulfide | 97 |

TABLE 2-continued

Reactions of Iodobenzene with Readily Available Thiophenols

| Entry | Thiol | Product | Isolated Yield (%) |
|---|---|---|---|
| 3 | 2-methylthiophenol | phenyl 2-methylphenyl sulfide | 95 |
| 4 | 4-methoxythiophenol | phenyl 4-methoxyphenyl sulfide | 95 |
| 5 | 2-methoxythiophenol | phenyl 2-methoxyphenyl sulfide | 94 |
| 6 | 3,5-dimethylthiophenol | phenyl 3,5-dimethylphenyl sulfide | 97 |
| 7 | 2,6-dimethylthiophenol | phenyl 2,6-dimethylphenyl sulfide | 95 |

TABLE 3

Reactions of Aryl Iodides with Readily Available Alkyl Thiols

| Entry | Aryl Iodide | Product | Isolated Yield (%) |
|---|---|---|---|
| 1 | iodobenzene | phenyl butyl sulfide | 95 |
| 2 | 4-iodotoluene | 4-methylphenyl butyl sulfide | 94 |

TABLE 3-continued

Reactions of Aryl Iodides with Readily Available Alkyl Thiols

R—[aryl]—I + Alkyl-SH →[CuI (10 mol %), Neocuproine (10 mol %), 1.5 eq. NaOt-Bu, Toluene, 110° C.] Ph-S-Alkyl

| Entry | Aryl Iodide | Product | Isolated Yield (%) |
|---|---|---|---|
| 3 | 2-iodotoluene | 2-methylphenyl butyl sulfide | 93 |
| 4 | 4-iodoanisole | 4-methoxyphenyl butyl sulfide | 95 |
| 5 | 2-iodoanisole | 2-methoxyphenyl butyl sulfide | 84 |
| 6 | 2-iodomesitylene | mesityl butyl sulfide | 98 |
| 7 | 1,4-diiodobenzene | 4-iodophenyl butyl sulfide | 88 |
| 8 | 1,4-diiodobenzene | 1,4-bis(butylthio)benzene | 98 |
| 9 | 1-bromo-4-iodobenzene | 4-bromophenyl butyl sulfide | 92 |
| 10 | 2-iodonaphthalene | 2-naphthyl butyl sulfide | 95 |
| 11 | 1-(4-iodophenyl)pyrrole | 1-(4-butylthiophenyl)pyrrole | 95 |
| 12 | iodobenzene | phenyl cyclohexyl sulfide | 77 |

In a similar manner, the cross-coupling reaction between aryl iodides and phenyl selenol was initially investigated using 10 mol % CuI/neocuproine with NaOt-Bu as the base and toluene as the solvent. Using this protocol, in 24 h, the reaction between iodobenzene and phenyl selenol was complete. If in the reaction protocol neocuproine was replaced by phenanthroline, diphenyl selenide was obtained in a lower yield (70% by GC). Moreover, the reaction with the well-defined complex Cu-(neocuproine)(PPh$_3$)Br showed complete conversion to the product after the same period of time. Use of CuI/neocuproine as catalyst, instead of the well-defined Cu(neocuproine)(PPh$_3$)Br, dispenses with the need to synthesize the complex and the results are comparable. The effect of the base on such reactions (see Table 4).

TABLE 4

Optimization of the reaction between aryl iodide and phenyl selenol

| Entry | Base | GC yield (1%) |
|---|---|---|
| 1 | CsF | <5 |
| 2 | Cs$_2$CO$_3$ | <5 |
| 3 | KOt-Bu | <10 |
| 4 | K$_2$CO$_3$ | 70 |
| 5 | Na$_2$CO$_3$ | 70 |
| 6 | K$_3$PO$_4$ | 82 |
| 7 | NaOt-Bu | 92 |

Sodium tert-butoxide was observed the most effective base for this reaction under the conditions employed. In contrast, KOt-Bu was not an effective base in this protocol, similar to what we had observed for the formation of aryl-sulfur bonds. Milder bases such as K$_3$PO$_4$, K$_2$CO$_3$ and Na$_2$CO$_3$ provided diphenyl selenide in moderate yields. Other mild bases such as CsF and Cs$_2$CO$_3$ were ineffective. In this protocol, iodobenzene was replaced with bromobenzene. By GC, in addition to both the starting materials, significant amount of diphenyl diselenide was observed, presumably from the oxidation of phenyl selenol. This indicated that the reaction was selective to iodides.

Using this protocol (see example 4 below), phenyl selenol was coupled with electron-rich aryl iodides in very good yields (Table 5). Sterically hindered iodides such as those with ortho-functionalities (entries 3, 5, 7 and 11), were coupled, as well as aryl iodides containing heteroatoms (entry 8 and 10). When o-iodoaniline was used as the aryl halide, in addition to the desired selenide, products were observed arising from the self-coupling of o-iodoaniline. This problem also persisted with K$_3$PO$_4$. However, when K$_2$CO$_3$ was used as the base, 1-amino-2-phenylselanyl-benzene was isolated in 60% yield (entry 12). With electron-poor aryl iodides, in addition to the desired diaryl selenides, diaryl diselenides were observed if NaOt-Bu or K$_3$PO$_4$ was used. In addition, with NaOt-Bu, transesterifcation products were observed when aryl halides with ester groups were used. Such complications can be avoided if K$_2$CO$_3$ is used instead of NaOt-Bu or K$_3$PO$_4$. Using this modified protocol a variety of diaryl selenides were obtained from electron-poor aryl halides (Table 6). The protocol tolerates even base sensitive groups such as esters and ketones (entries 3, 4, and 6).

TABLE 5

Reaction of electron-rich aryl iodides and phenyl selenol

| Entry | Aryl Iodide | Product | Isolated Yield (%) |
|---|---|---|---|
| 1 | [phenyl iodide] | [diphenyl selenide] | 90 |
| 2 | [4-methylphenyl iodide] | [4-methylphenyl phenyl selenide] | 84 |
| 3 | [2-methylphenyl iodide] | [2-methylphenyl phenyl selenide] | 80 |
| 4 | [4-methoxyphenyl iodide] | [4-methoxyphenyl phenyl selenide] | 88 |
| 5 | [2-methoxyphenyl iodide] | [2-methoxyphenyl phenyl selenide] | 78 |

TABLE 5-continued

Reaction of electron-rich aryl iodides and phenyl selenol

| Entry | Aryl Iodide | Product | Isolated Yield (%) |
|---|---|---|---|
| 6 | 4-(n-butyl)phenyl iodide | 4-(n-butyl)phenyl phenyl selenide | 80 |
| 7 | 2-iodo-1,3,5-trimethylbenzene | (2,4,6-trimethylphenyl)(phenyl)selenide | 82 |
| 8 | 2-iodothiophene | 2-(phenylselanyl)thiophene | 68 |
| 9 | 1-iodonaphthalene | 1-(phenylselanyl)naphthalene | 82 |
| 10 | 1-(4-iodophenyl)-1H-pyrrole | 1-(4-(phenylselanyl)phenyl)-1H-pyrrole | 76 |
| 11 | 1,2-diiodobenzene | 1,2-bis(phenylselanyl)benzene | 81 |
| 12 | 2-iodoaniline | 2-(phenylselanyl)aniline | 60* |

*K$_2$CO$_3$ was used instead of NaOt-Bu as the base. For all entries, catalyst loading: 10 mol % CuI & 10 mol % neocuproine, solvent: toluene, temperature: 110° C.

TABLE 6

Reaction of electron-poor aryl iodides and phenyl selenol

| Entry* | Aryl Iodide | Product | Isolated Yield (%) |
|---|---|---|---|
| 1 | 1-iodo-4-nitrobenzene | 1-nitro-4-(phenylselanyl)benzene | 75 |

TABLE 6-continued

Reaction of electron-poor aryl iodides and phenyl selenol

| Entry* | Aryl Iodide | Product | Isolated Yield (%) |
|---|---|---|---|
| 2 | 2-iodonitrobenzene | 2-(phenylselanyl)nitrobenzene | 81 |
| 3 | methyl 4-iodobenzoate | methyl 4-(phenylselanyl)benzoate | 78 |
| 4 | methyl 2-iodobenzoate | methyl 2-(phenylselanyl)benzoate | 76 |
| 5 | 1-fluoro-4-iodobenzene | 1-fluoro-4-(phenylselanyl)benzene | 92 |
| 6 | 1-(4-iodophenyl)ethanone | 1-(4-(phenylselanyl)phenyl)ethanone | 78 |

*For all entries, catalyst loading: 10 mol % CuI & 10 mol % neocuproine, solvent: toluene, temperature: 110° C.

As shown above and supported below, the present invention provides a general synthetic methodology for the formation of aryl-sulfur bonds, using copper(I) catalysts. While efficacy was shown generally over a broad range of substrate starting materials using 10 mol % CuI, 10 mol % neocuproine, NaOt-Bu as the base and toluene as the solvent, other Cu(I) halides, ligands, bases and solvents can be used depending upon a particular desired reaction system, in a straight-forward manner without undue experimentation. In cases where NaOt-Bu cannot be used, alternate bases include $K_3PO_4$. The methodology is palladium-free and avoids the use of expensive and/or air-sensitive ligands and can be readily adapted to current synthetic operations.

Likewise, the present invention provides a general synthetic protocol for the formation of diaryl selenides, using copper(I) catalysts and, optimally, 10 mol % CuI, 10 mol % neocuproine, NaOt-Bu as the base, with toluene as the solvent for electron-rich aryl iodides. For electron-poor aryl iodides, the use of $K_2CO_3$ is recommended in the place of NaOt-Bu. The protocol is palladium-free and avoids the use of expensive and/or air-sensitive ligands, and makes use of readily available phenyl selenols.

Consistent with and as a straightforward extension of the foregoing, this invention can be used in conjunction with the synthesis of vinyl sulfides via the cross-coupling of vinyl halides (e.g., iodides and bromides) and thiols. Yields of the desired product are in the range of 90–99%. Depending on reactants, certain embodiments effectively use Cu(phen)(PPh$_3$)$_2$NO$_3$ as a Cu(I) compound and $K_3PO_4$ as a base in toluene, or CuI/neocuproine and $K_3PO_4$ in isopropyl alcohol.

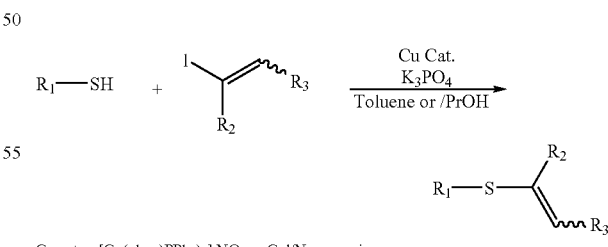

Cu cat. = [Cu(phen)PPh$_3$)$_2$] NO$_3$ or CuI/Neocuproine

Without limitation, any of the aforementioned thiols (e.g., thiols of Tables 2 and 3) can be coupled to commercially or synthetically available vinyl halides. See, e.g., the thiols and vinyl halides of FIGS. 3A–D. Such methods of this invention are illustrated in the following examples.

EXAMPLES OF THE INVENTION

The following non-limiting examples and data illustrate various aspects and features relating to the methodologies of the present invention, including the preparation of a range of aryl-sulfur compounds, as are available using the catalytic systems described herein. In comparison with the prior art, the present methods, catalysts and/or catalytic systems provide results and data which are surprising, unexpected and contrary to the prior art. While the utility of this invention is illustrated through the use of several aryl halides, aryl or alkyl thiols and Cu(I) catalysts which can be used therewith, it will be understood by those skilled in the art that comparable results are obtainable with various other aryl halides, thiols and Cu(I) metal-ligand compounds, as are commensurate with the scope of this invention.

General. All of the reactions reported herein were conducted under an inert atmosphere of argon in oven-dried glassware. All reagents and solvents were obtained from Acros or from Aldrich and were used without further purification. Sodium tert-Butoxide (Acros, 99%) was stored in an argon filled glove box. Purification was performed by flash chromatography using ICN Flash Silica Gel, 230–400 mesh. The yields given refer to isolated yields of the characterized compounds, deemed pure by elemental analyses, $^1$H NMR and $^{13}$C NMR. NMR spectra were recorded on a Bruker AVANCE 300 MHz spectrometer. Chemical shifts were reported in parts per million ($\delta$). The peak patterns are indicated as follows: s, singlet; d, doublet; t, triplet; dd, doublet of doublets; dt, doublet of triplets; and m, multiplet. The coupling constants, J, are reported in Hertz (Hz). The residual solvent peak was used as the internal reference. All proton and $^{13}$C NMR assignments for the diphenylsulfides were made using the work done by Perumal et. al. (*Magn. Reson. Chem.* 1987, 25, 1001–1006; *Magn. Reson. Chem.* 1995, 33, 779–790.) as a reference. Elemental analyses were performed at the Microanalysis Laboratory, University of Massachusetts at Amherst. The reported melting points were uncorrected.

Example 1

Cu-Catalyzed Coupling of thiophenols with aryl iodides

General Procedure: In an argon-filled glove box, a Pyrex glass tube (2.5 cm in diameter) equipped with a Teflon stir bar, was charged with sodium tert-butoxide (Acros, 3.0 mmol), CuI (10 mol % with respect to the aryl iodide), and neocuproine (10 mol % with respect to the aryl iodide). The tube was then sealed with a rubber septum, taken out of the glove box and thiophenol (2.2 mmol), the aryl iodide (2.00 mmol) and toluene (6.0 mL) were injected into the tube through the septum. The contents were then stirred at 110° C. for 24 hours. The reaction mixture was then cooled to room temperature and filtered to remove any insoluble residues. The filtrate was concentrated in vacuo; the residue was purified by flash column chromatography on silica gel to obtain the analytically pure product. Due to the stench of the thiols, all glassware and syringes used were washed with bleach to reduce the odor of the thiols.

Example 1a p-Tolylthiophenol (entry 1, Table 1): The general procedure was used to convert 4-iodotoluene and thiophenol to the title product. Purification by flash chromatography (hexane as the eluent) gave the analytically pure product as a clear oil (379 mg, 94% yield). $^1$H NMR (300 MHz, CDCl$_3$) $\delta$ 7.22–7.08 (m, 7H; H$_a$, H$_{a'}$, H$_c$, H$_{c'}$, H$_d$, H$_{d'}$, H$_e$) 7.04–7.00 (d, J=7.91, 2H; H$_b$, H$_{b'}$), 2.25 (s, 3H; methyl protons). $^{13}$C NMR (75 MHz, CDCl$_3$) $\delta$ 137.54 (C$_4$), 137.09 (C$_{1'}$), 132.24 (C$_2$, C$_6$), 131.24 (C$_1$), 130.03 (C$_3$, C$_5$), 129.72 (C$_{2'}$, C$_{6'}$), 128.99 (C$_{3'}$, C$_{5'}$), 126.35 (C$_{4'}$), 21.09 (C$_7$). Anal. Calcd. for C$_{13}$H$_{12}$S: C, 77.95; H, 6.04; S, 16.01; Found C, 78.00; H, 6.06; S, 15.88.

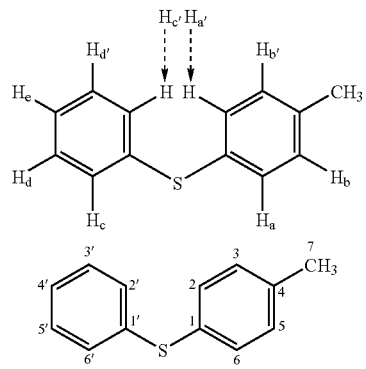

Example 1b o-Tolylthiophenol (entry 2, Table 1): The general procedure was used to convert 2-iodotoluene and thiophenol to the title product. Purification by flash chromatography (hexane as the eluent) gave the analytically pure product as a clear oil (386 mg, 96% yield). $^1$H NMR (300 MHz, CDCl$_3$) $\delta$ 7.20–7.00 (m, 9H; H$_a$, H$_b$, H$_c$, H$_d$, H$_e$, H$_{e'}$, H$_f$, H$_{f'}$, H$_g$), 2.26 (s, 3H; methyl protons). $^{13}$C NMR (75 MHz, CDCl$_3$) $\delta$ 139.88 (C$_8$), 136.08 (C$_6$), 133.69 (C$_1$), 132.93 (C$_2$), 130.54 (C$_5$), 129.55 (C$_9$, C$_{13}$), 129.07, (C$_{10}$, C$_{12}$), 127.84 (C$_3$), 126.66 (C$_{11}$), 126.27 (C$_4$), 20.55 (C$_7$). Anal. Calcd. for C$_{13}$H$_{12}$S: C, 77.95; H, 6.04; S, 16.01; Found C, 77.87; H, 6.06; S, 15.81.

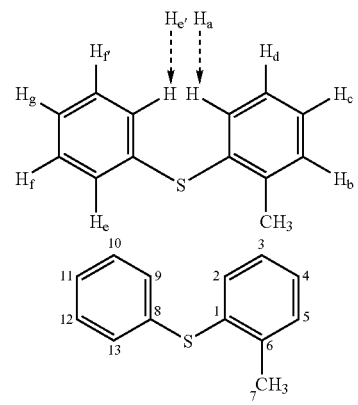

Example 1c

1-Methoxy-4-(phenylthio)benzene (entry 3, Table 1): The general procedure was used to convert 4-iodoanisole and thiophenol to the title product. Purification by flash chromatography (hexane/CH$_2$Cl$_2$ [3:1] as the eluent) gave the analytically pure product as a clear oil (416 mg, 96% yield). $^1$H NMR (300 MHz, CDCl$_3$) δ 7.29 (dt, J=7.72, 2H; H$_a$, H$_{a'}$), 7.13–6.97 (m, 5H; H$_c$, H$_{c'}$, H$_d$, H$_{d'}$, H$_e$), 6.77 (d, J=7.54, 2H; H$_b$, H$_{b'}$), 3.67 (s, 3H; methyl protons). $^{13}$C NMR (75 MHz, CDCl$_3$) δ 159.74 (C$_4$), 138.54 (C$_8$), 135.29 (C$_2$, C$_6$), 128.85 (C$_9$, C$_{13}$), 128.08 (C$_{10}$, C$_{12}$), 125.66 (C$_{11}$), 124.17 (C$_1$), 114.90 (C$_3$, C$_5$), 55.23 (C$_7$). Anal. Calcd. for C$_{13}$H$_{12}$OS: C, 72.19; H, 5.59; S, 14.82; Found C, 72.34; H, 5.70; S, 14.81.

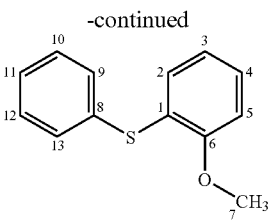

Example 1e

4-Phenylsulfanyl-benzoic acid methyl ester (entry 5, Table 1): The general procedure was used to convert Methyl-4-iodobenzoate and thiophenol to the title product. Purification by flash chromatography (hexane/ethyl acetate [6:1] as the eluent) gave the analytically pure product as a white solid (411 mg, 84% yield). $^1$H NMR (300 MHz, CDCl$_3$) δ 7.88 (dt, J=8.67, 2H; H$_b$, H$_{b'}$), 7.51–7.47 (m, 2H; H$_c$, H$_{c'}$), 7.39–7.37 (m, 3H; H$_d$, H$_{d'}$, H$_e$), 7.21 (dt, J=8.67, 2H; H$_a$, H$_{a'}$), 3.89 (s, 3H; methyl protons). $^{13}$C NMR (75 MHz, CDCl$_3$) δ 166.60 (C$_{13}$), 144.33 (C$_1$), 133.63 (C$_4$), 132.29 (C$_8$, C$_{12}$), 130.03 (C$_7$), 129.58 (C$_9$, C$_{11}$), 128.60 (C$_3$, C$_5$), 127.47 (C$_{10}$), 127.39 (C$_2$, C$_6$), 52.02 (C$_{14}$). Anal. Calcd. for C$_{14}$H$_{12}$O$_2$S: C, 68.83; H, 4.95; S, 13.13; Found C, 68.87; H, 4.95; S, 12.96. mp found: 70–71° C.

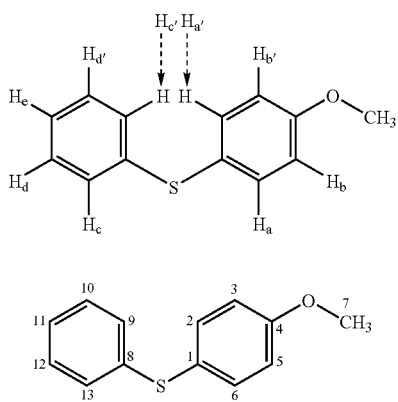

Example 1d

1-Methoxy-2-(phenylthio)benzene (entry 4, Table 1): The general procedure was used to convert 2-iodoanisole and thiophenol to the title product. Purification by flash chromatography (hexane/CH$_2$Cl$_2$ [3:1] as the eluent) gave the analytically pure product as a clear oil (412 mg, 95% yield). $^1$H NMR (300 MHz, CDCl$_3$) δ 7.41–7.25 (m, 6H; H$_c$, H$_e$, H$_{e'}$, H$_f$, H$_{f'}$, H$_g$), 7.12 (dd, J=6.03, 1H; H$_a$), 6.96–6.89 (m, 2H; H$_b$, H$_d$), 3.90 (s, 3H; methyl protons). $^{13}$C NMR (75 MHz, CDCl$_3$) δ 157.21 (C$_6$), 134.39 (C$_8$), 131.50 (C$_2$), 131.35 (C$_9$, C$_{13}$), 129.07 (C$_{10}$, C$_{12}$), 128.27 (C$_4$), 126.99 (C$_{11}$), 123.96 (C$_1$), 121.16 (C$_3$), 110.76 (C$_5$), 55.78 (C$_7$). Anal. Calcd. for C$_{13}$H$_{12}$OS: C, 72.19; H, 5.59; S, 14.82; Found C, 72.23; H, 5.70; S, 14.67.

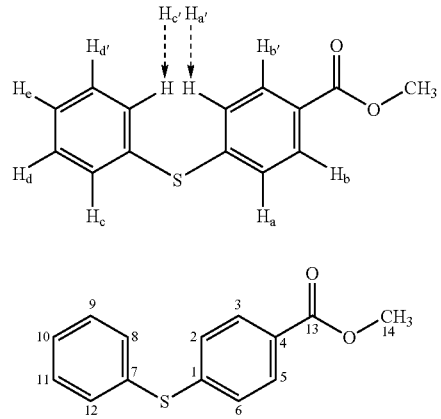

Example 1f

2-Phenylsulfanyl-benzoic acid methyl ester (entry 6, Table 1): The general procedure was used to convert Methyl-2-iodobenzoate and thiophenol to the title product. Purification by flash chromatography (hexane/ethyl acetate [6:1] as the eluent) gave the analytically pure product as a clear oil (397 mg, 81% yield). $^1$H NMR (300 MHz, CDCl$_3$) δ 7.88 (dd, J=6.22, 1H; H$_d$), 7.47 (m, 2H; H$_a$, H$_b$), 7.33 (m, 3H; H$_e$, H$_{e'}$, H$_f$), 7.14 (td, J=5.4, 1H; H$_c$), 7.04 (td, J=6.02, 1H; H$_f$), 6.73 (dd, J=6.78, 1H; H$_g$), 3.85 (s, 3H; methyl protons). $^{13}$C NMR (75 MHz, CDCl$_3$) δ 166.79 (C$_{13}$), 143.15 (C$_1$), 135.47 (C$_6$), 132.39 (C$_3$), 132.22 (C$_2$), 130.93 (C$_5$), 129.65 (C$_7$), 129.02 (C$_8$, C$_{12}$), 127.28 (C$_9$, C$_{11}$), 126.58 (C$_{10}$), 124.19 (C$_4$), 52.10 (C$_{14}$). Anal. Calcd. for C$_{14}$H$_{12}$O$_2$S: C, 68.83; H, 4.95; S, 13.13; Found C, 68.94; H, 5.10; S, 12.90.

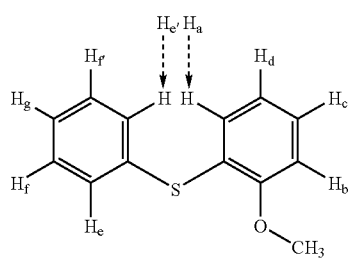

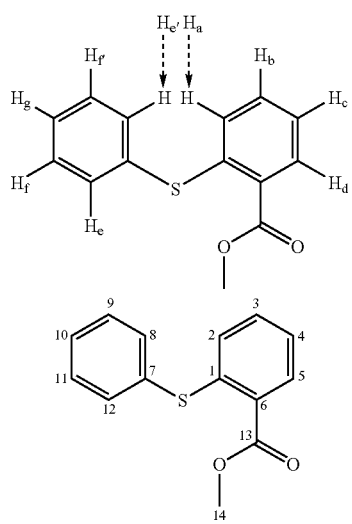

Example 1g (2,4,6-trimethyl-phenyl)-phenyl sulfide (entry 7, Table 1): The general procedure was used to convert 2,4,6-trimethyliodobenzene and thiophenol to the title product. Purification by flash chromatography (hexane as the eluent) gave the analytically pure product as a clear oil (444 mg, 97% yield). $^1$H NMR (300 MHz, CDCl$_3$) δ 7.20 (m, 2H; H$_b$, H$_{b'}$), 7.09 (m, 3H; H$_c$, H$_{c'}$, H$_d$), 6.96 (m, 2H; H$_a$, H$_{a'}$) 2.44 (s, 6H; ortho methyl protons), 2.37 (s, 3H, para methyl protons). $^{13}$C NMR (75 MHz, CDCl$_3$) δ 143.67 (C$_2$, C$_6$), 139.21 (C$_4$), 138.35 (C$_1$), 129.29 (C$_{10}$), 128.81 (C$_{11}$, C$_{15}$), 127.20 (C$_{12}$, C$_{14}$), 125.39 (C$_3$, C$_5$), 124.41 (C$_{13}$), 21.67 (C$_7$, C$_8$), 21.10 (C$_9$). Anal. Calcd. for C$_{15}$H$_{16}$S: C, 78.90; H, 7.06; S, 14.04; Found C, 78.76; H, 7.23; S, 14.10.

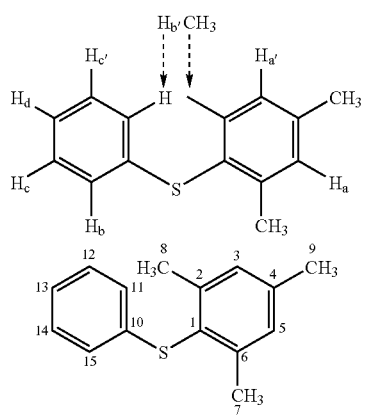

Example 1h

2-Phenylsulfanyl-phenol (entry 8, Table 1): The general procedure was used to convert 2-iodothiophene and thiophenol to the title product. Purification by flash chromatography (hexane/ethyl acetate (6:1) as the eluent) gave the analytically pure product as a light brown oil (328 mg, 81% yield). $^1$H NMR (300 MHz, CDCl$_3$) δ 7.43 (dd, J=5.65, 1H; H$_{e'}$), 7.28 (m, 1H; H$_e$), 7.14 (m, 2H; H$_f$, H$_{f'}$), 7.07–6.97 (m, 4H; H$_a$, H$_b$, H$_c$, H$_g$), 6.86 (td, J=6.02, 1H; H$_{d'}$), 6.44 (s, 1H, alcohol proton). $^{13}$C NMR (75 MHz, CDCl$_3$) δ 157.22 (C$_6$), 136.89 (C$_2$), 135.80 (C$_7$), 132.26 (C$_8$, C$_{12}$), 129.17 (C$_9$, C$_{11}$), 126.78 (C$_4$), 126.07 (C$_{10}$), 121.25 (C$_3$), 116.20 (C$_1$), 115.51 (C$_5$). Anal. Calcd. for C$_{12}$H$_{10}$S: C, 71.25; H, 4.98; S, 15.85; Found C, 71.25; H, 5.01; S, 15.82.

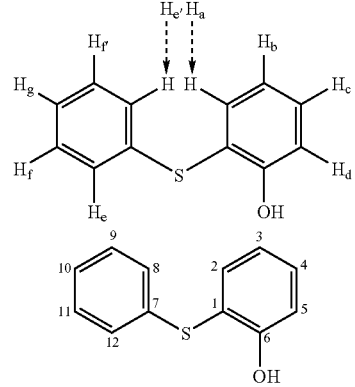

Example 1i

2-Phenylsulfanyl-thiophene (entry 9, Table 1): The general procedure was used to convert 2-iodophenol and thiophenol to the title product. Purification by flash chromatography (hexane as the eluent) gave the analytically pure product as a clear oil (349 mg, 91% yield). $^1$H NMR (300 MHz, CDCl$_3$) δ 7.52 (dd, J=4.14, 2H; H$_a$, H$_{a'}$), 7.36–7.21 (m, 6H; H$_b$, H$_{b'}$, H$_c$, H$_d$, H$_f$), 7.12 (m, 1H; H$_e$). $^{13}$C NMR (75 MHz, CDCl$_3$) δ 138.59 (C$_1$), 136.03 (C$_7$), 131.24 (C$_2$, C$_6$), 131.02 (C$_9$), 128.91 (C$_3$, C$_5$), 127.88 (C$_8$), 127.03 (C$_{10}$), 125.98 (C$_4$). Anal. Calcd. for C$_{10}$H$_8$S$_2$: C, 62.46; H, 4.19; S, 33.35; Found C, 62.56; H, 4.21; S, 33.13.

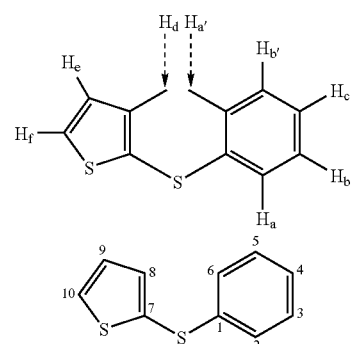

Example 2a

Diphenylsulfide (entry 1, Table 2): The general procedure was used to convert iodobenzene and thiophenol to the title product. Purification by flash chromatography (hexane as the eluent) gave the analytically pure product as a clear oil (360 mg, 98% yield). $^1$H NMR (300 MHz, CDCl$_3$) δ 7.48–7.44 (m, 4H; H$_a$, H$_{a'}$, H$_d$, H$_{d'}$), 7.42–7.39 (m, 4H; H$_b$, H$_{b'}$, H$_e$, H$_{e'}$), 7.37–7.31 (m, 2H; H$_c$, H$_{c'}$). $^{13}$C NMR (75 MHz, CDCl$_3$) δ 135.70 (C$_1$), 130.94 (C$_2$), 129.10 (C$_3$), 126.94 ($C_4$). Anal. Calcd. for $C_{12}H_{10}S$: C, 77.37; H, 5.41; S, 17.21; Found C, 77.50; H, 5.45; S, 17.00.

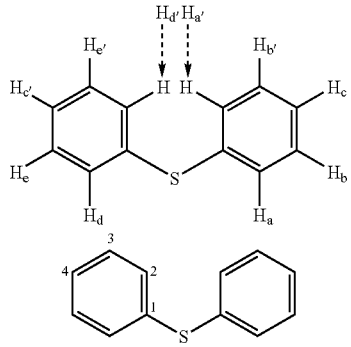

Example 2b p-Tolylthiophenol (entry 2, Table 2): The general procedure was used to convert iodobenzene and p-toluenethiol to the title product. Purification by flash chromatography (hexane as the eluent) gave the analytically pure product as a clear oil (388 mg, 97.0% yield). $^1$H NMR (300 MHz, CDCl$_3$) δ 7.18 (dt, J=8.1, 2H; $H_a$, $H_{a'}$), 7.15–7.12 (m, 4H; $H_e$, $H_{e'}$, $H_f$, $H_{f'}$), 7.08 (m, 1H; $H_g$), 7.04–7.00 (d, J=7.34, 2H; $H_c$, $H_{c'}$), 2.22 (s, 3H; methyl protons). $^{13}$C NMR (75 MHz, CDCl$_3$) δ 138.05 ($C_4$), 137.62 ($C_{1'}$), 132.77 ($C_2$, $C_6$), 131.76 ($C_1$), 130.55 ($C_3$, $C_5$), 130.23 ($C_{2'}$, $_{C6'}$), 129.52 ($C_{3'}$, $C_{5'}$), 126.87 ($C_{4'}$), 21.62 ($C_7$). Anal. Calcd. for $C_{13}H_{12}S$: C, 77.95; H, 6.04; S, 16.01; Found C, 77.78; H, 6.01; S, 16.19.

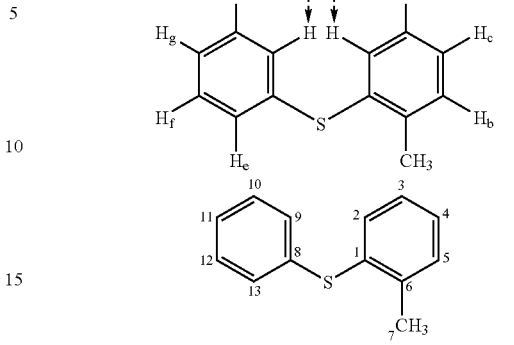

Example 2d

1-Methoxy-4-(phenylthio)benzene (entry 4, Table 2): The general procedure was used to convert iodobenzene and 4-methoxybenzenethiol to the title product. Purification by flash chromatography (hexane/CH$_2$Cl$_2$ [3:1] as the eluent) gave the analytically pure product as a clear oil (410 mg, 95% yield). $^1$H NMR (300 MHz, CDCl$_3$) δ 7.27 (dt, J=8.85, 2H; $H_a$, $H_{a'}$), 7.12–6.96 (m, 5H; HC, $H_{c'}$, $H_d$, $H_{d'}$, $H_e$), 6.75 (dt, 2H; $H_b$, $H_{b'}$), 3.67 (s, 3H; methyl protons). $^{13}$C NMR (75 MHz, CDCl$_3$) δ 159.76 ($C_4$), 138.56 ($C_8$), 135.32 ($C_2$, $C_6$), 128.86 ($C_9$, $C_{13}$), 128.10 ($C_{10}$, $C_{12}$), 125.68 ($C_{11}$), 124.19 ($C_1$), 114.92 ($C_3$, $C_5$), 55.27 ($C_7$). Anal. Calcd. for $C_{13}H_{12}OS$: C, 72.19; H, 5.59; S, 14.82; Found C, 72.26; H, 5.59; S, 14.65.

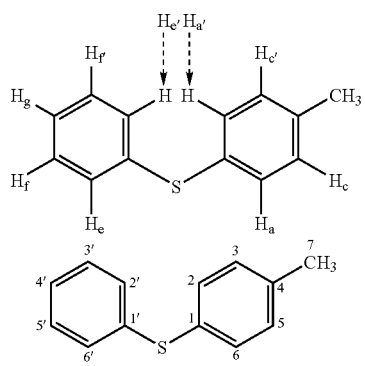

Example 2c o-Tolylthiophenol (entry 3, Table 2): The general procedure was used to convert iodobenzene and o-toluenethiol to the title product. Purification by flash chromatography (hexane as the eluent) gave the analytically pure product as a clear oil (383 mg, 95% yield). $^1$H NMR (300 MHz, CDCl$_3$) δ 7.20–6.98 (m, 9H; $H_a$, $H_b$, $H_c$, $H_d$, $H_e$, $H_{e'}$, $H_f$, $H_{f'}$, $H_g$), 2.27 (s, 3H; methyl protons). $^{13}$C NMR (75 MHz, CDCl$_3$) δ 139.90 ($C_8$), 136.10 ($C_6$), 133.70 ($C_1$), 132.94 ($C_2$), 130.54 ($C_5$), 129.55 ($C_9$, $C_{13}$), 129.07, ($C_{10}$, $C_{12}$), 127.85 ($C_3$), 126.66 ($C_{11}$), 126.27 ($C_4$), 20.54 ($C_7$). Anal. Calcd. for $C_{13}H_{12}S$: C, 77.95; H, 6.04; S, 16.01; Found C, 78.02; H, 6.01; S, 16.01.

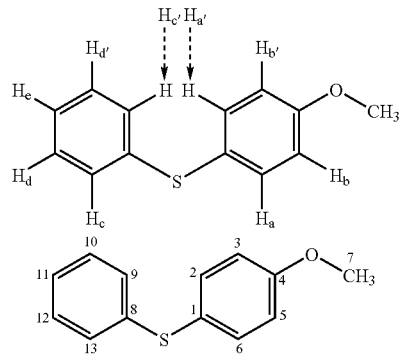

Example 2e

1-Methoxy-2-(phenylthio)benzene (entry 5, Table 2): The general procedure was used to convert iodobenzene and 2-methoxybenzenethiol to the title product. Purification by flash chromatography (hexane/CH$_2$Cl$_2$ [3:1] as the eluent) gave the analytically pure product as a clear oil (406 mg, 94% yield). $^1$H NMR (300 MHz, CDCl$_3$) δ 7.43–7.25 (m, 6H; $H_c$, $H_e$, $H_{e'}$, $H_f$$H_{f'}$, $H_g$), 7.14 (dd, 1H; Ha), 6.96–6.89 (m, 2H; $H_b$, $H_d$), 3.90 (s, 3H; methyl protons). $^{13}$C NMR (75 MHz, CDCl$_3$) δ 157.20 ($C_6$), 134.38 ($C_8$), 131.88 ($C_2$), 131.35 ($C_9$, $C_{13}$), 129.15 ($C_{10}$, $C_{12}$), 128.25 ($C_4$), 127.40 ($C_{11}$), 123.93 ($C_1$), 121.14 ($C_3$), 110.75 ($C_5$), 55.76 ($C_7$). Anal. Calcd. for $C_{13}H_{12}OS$: C, 72.19; H, 5.59; S, 14.82; Found C, 72.22; H, 5.70; S, 14.63.

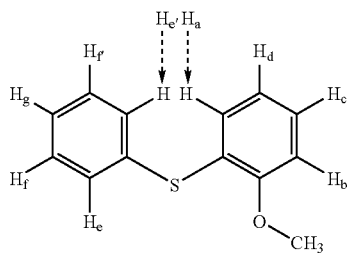

Example 2f (3,5-dimethyl-phenyl)-phenyl sulfide (entry 6, Table 2): The general procedure was used to convert iodobenzene and 3,5-dimethylthiophenol to the title product. Purification by flash chromatography (hexane as the eluent) gave the analytically pure product as a clear oil (417 mg, 97% yield). $^1$H NMR (300 MHz, CDCl$_3$) δ 7.17–7.01 (m, 5H; $H_c$, $H_{c'}$, $H_d$, $H_{d'}$, $H_e$), 6.84 (s, 2H; $H_a$, $H_{a'}$), 6.72 (s, 1H; $H_b$), 2.10 (s, 3H; methyl protons). $^{13}$C NMR (75 MHz, CDCl$_3$) δ 138.81 ($C_3$, $C_5$), 136.35 ($C_9$), 134.69 ($C_1$), 130.44 ($C_{10}$, $C_{14}$), 129.10 ($C_{11}$, $C_{13}$), 129.02 ($C_2$, $C_6$), 128.68 ($C_4$), 126.61 ($C_{12}$), 21.13 ($C_7$, $C_8$). Anal. Calcd. for $C_{14}H_{14}S$: C, 78.45; H, 6.58; S, 14.96; Found C, 78.53; H, 6.62; S, 14.89.

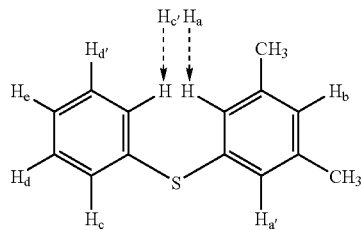

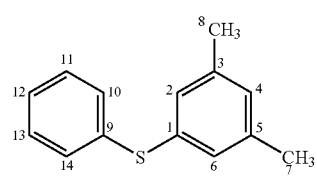

Example 2g (2,6-dimethyl-phenyl)-phenyl sulfide (entry 7, Table 2): The general procedure was used to convert iodobenzene and 2,6-dimethylthiophenol to the title product. Purification by flash chromatography (hexane as the eluent) gave the analytically pure product as a clear oil (409 mg, 95% yield). $^1$H NMR (300 MHz, CDCl$_3$) δ 7.1–6.98 (m, 5H; $H_c$, $H_{c'}$, $H_d$, $H_{d'}$, $H_e$), 6.93–6.86 (m, 1H; $H_b$), 6.77 (d, J=7.16, 2H; $H_a$, $H_{a'}$) 2.34 (s, 6H; methyl protons). $^{13}$C NMR (75 MHz, CDCl$_3$) δ 143.86 ($C_2$, $C_6$), 137.98 ($C_9$), 130.43 ($C_1$), 129.22 ($C_4$), 128.86 ($C_{10}$, $C_{14}$), 128.40 ($C_1$, $C_{13}$), 125.59 ($C_3$, $C_5$), 124.57 ($C_{12}$), 21.82 ($C_7$, $C_8$). Anal. Calcd. for $C_{14}H_{14}S$: C, 78.45; H, 6.58; S, 14.96; Found C, 78.58; H, 6.71; S, 14.98.

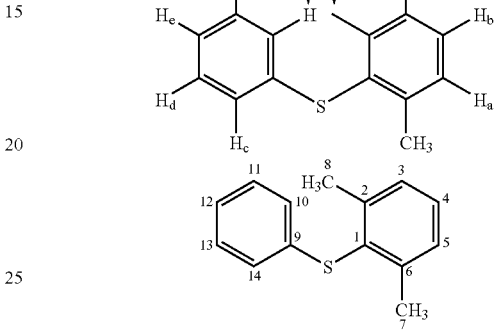

Example 3

Cu-Catalyzed Coupling of n-Butyl sulfides with aryl iodides.

General Procedure: In an argon-filled glove box, a Pyrex glass tube (2.5 cm in diameter) equipped with a Teflon stir bar, was charged with sodium tert-butoxide (Acros, 3.0 mmol), CuI (10 mol % with respect to the aryl iodide), and neocuproine (10 mol % with respect to the aryl iodide). The tube was then sealed with a rubber septum, taken out of the glove box and n-butyl sulfide (2.2 mmol), the aryl iodide (2.00 mmol) and toluene (5.0 mL) were injected into the tube through the septum. The contents were then stirred at 110° C. for 24 hours. The reaction mixture was then cooled to room temperature and filtered to remove any insoluble residues. The filtrate was concentrated in vacuo; the residue was purified by flash column chromatography on silica gel to obtain the analytically pure product. Due to the stench of the n-butyl sulfides, all glassware and syringes used were washed with bleach to reduce the odor of the thiols.

Example 3a n-Butyl Phenyl Sulfide (entry 1, Table 3): The general procedure was used to convert iodobenzene and n-butyl sulfide to the title product. Purification by flash chromatography (hexane as the eluent) gave the analytically pure product as a clear oil (310 mg, 95% yield). $^1$H NMR (300 MHz, CDCl$_3$) δ 7.26–7.09 (m, 5H; $H_b$, $H_{b'}$, $H_c$, $H_{c'}$, $H_d$), 2.88–2.82 (t, J=4.0, 2H; $H_e$), 1.60–1.46 (m, 2H; $H_f$), 1.42–1.30 (m, 2H; $H_g$), 0.88–0.82 (t, J=3.9, 3H; methyl protons). $^{13}$C NMR (75 MHz, CDCl$_3$) δ 136.9 ($C_1$), 128.7 ($C_3'$, $C_3$, $C_2$, $C_2'$), 125.5 ($C_4$), 33.1 ($C_5$), 31.1 ($C_6$), 21.9 ($C_7$), 13.6 ($C_8$). Anal. Calcd. for $C_{10}H_{14}S$: C, 72.23; H, 8.49; S, 19.28; Found C, 71.97; H, 8.67; S, 19.07.

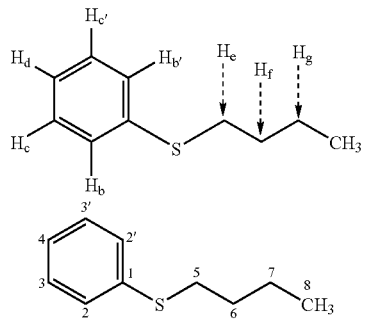

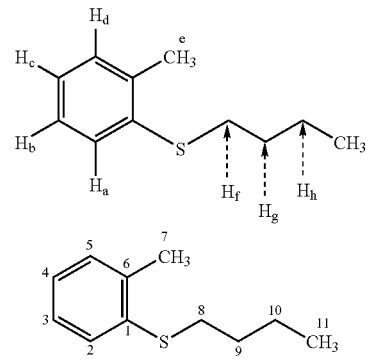

Example 3b n-Butyl 4-Methylphenyl Sulfide (entry 2, Table 3): The general procedure was used to convert 4-iodotoluene and n-butyl sulfide to the title product. Purification by flash chromatography (hexane as the eluent) gave the analytically pure product as a clear oil (331 mg, 94% yield). $^1$H NMR (300 MHz, CDCl$_3$) δ 7.15–7.12 (d, J=8.2, 2H; H$_a$, H$_{a'}$), 6.98–6.96 (d, J=7.9, 2H; H$_b$, H$_{b'}$), 2.79–2.74 (t, J=7.1, 2H; H$_c$), 2.20 (Methyl Protons), 1.55–1.45 (m, 2H; H$_d$), 1.39–1.15 (m, 2H; H$_e$), 0.83–0.78 (t, J=7.1, 3H; H$_f$). $^{13}$C NMR (75 MHz, CDCl$_3$) δ 135.6 (C$_4$), 133 (C$_3$), 129.6 (C$_1$, C$_{1'}$), 129.47 (C$_2$, C$_2$), 33.8 (methyl protons), 31.2 (C$_5$), 21.8 (C$_6$), 20.8 (C$_7$), 13.54 (C$_8$). Anal. Calcd. for C$_{11}$H$_{16}$S: C, 73.27; H, 8.94; S, 17.78; Found C, 73.21; H, 9.15; S, 17.57.

Example 3d n-Butyl 4-Methoxyphenyl Sulfide (entry 4, Table 3): The general procedure was used to convert 4-methoxy iodobenzene and n-butyl sulfide to the title product. Purification by flash chromatography (hexane as the eluent) gave the analytically pure product as a clear oil (370 mg, 95% yield). $^1$H NMR (300 MHz, CDCl$_3$) δ 7.26–7.23 (d, J=9.0. 2H; H$_b$, H$_{b'}$), 6.76–6.73 (d, J=8.8, 2H; H$_c$, H$_{c'}$), 3.69 (s, 3H; H$_g$), 2.75–2.70 (t, 2H; H$_d$), 1.50–1.43 (m, 2H; H$_e$), 1.36–1.28 (m, 2H; H$_f$), 0.83–0.78 (t, 3H; methyl protons). $^{13}$C NMR (75 MHz, CDCl$_3$) δ 158.62 (C$_4$), 132.81 (C$_1$), 126.85 (C$_2$, C$_2$), 114.39 (C$_3$, C$_3$), 55.21 (C$_9$), 35.04 (C$_5$), 31.63 (C$_6$), 21.75 (C$_7$), 13.59 (C$_8$). Anal. Calcd. for C$_{11}$H$_{16}$SO: C, 67.30; H, 8.22; S, 16.33; Found C, 66.87; H, 8.28; S, 16.21.

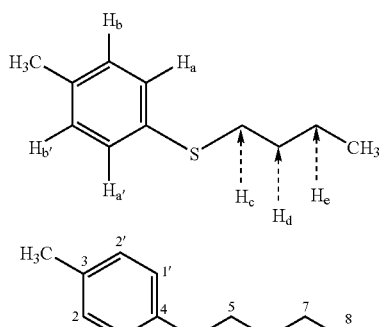

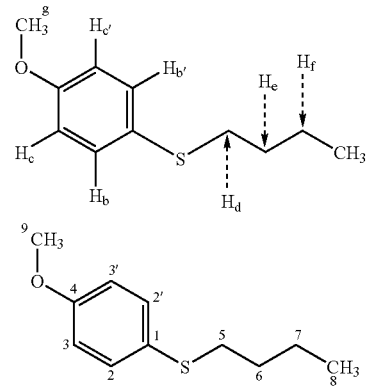

Example 3c n-Butyl 2-Methylphenyl Sulfide (entry 3, Table 3): The general procedure was used to convert 2-iodotoluene and n-butyl sulfide to the title product. Purification by flash chromatography (hexane as the eluent) gave the analytically pure product as a clear oil (331 mg, 93% yield). $^1$H NMR (300 MHz, CDCl$_3$) δ 7.17–6.97 (m, 4H; H$_a$, H$_b$, H$_c$, H$_d$), 2.80–2.78 (t, J=7.3, 2H; H$_f$), 2.27 (s, 3H; H$_e$), 1.61–1.51 (m, 2H; H$_g$), 1.44–1.17 (m, 2H; H$_h$), 0.87–0.82 (t, J=7.3, 3H; methyl protons). $^{13}$C NMR (75 MHz, CDCl$_3$) δ 137 (C$_1$), 136.3 (C$_6$), 129.9 (C$_5$), 127.1 (C$_2$), 126.2 (C$_3$), 125.1 (C$_4$), 32.3 (C$_8$), 31 (C$_9$), 22 (C$_{10}$), 20.2 (C$_7$), 13.6 (C$_{11}$). Anal. Calcd. for C$_{11}$H$_{16}$S: C, 73.27; H, 8.94; S, 17.78; Found C, 73.23; H, 9.16, S, 17.57.

Example 3e n-Butyl 2-Methoxyphenyl Sulfide (entry 5, Table 3): The general procedure was used to convert 2-iodoanisole and n-butyl sulfide to the title product. Purification by flash chromatography (hexane as the eluent) gave the analytically pure product as a light yellow oil (329 mg, 84% yield). $^1$H NMR (300 MHz, CDCl$_3$) δ 7.18–6.75 (m, 4H; H$_b$, H$_c$, H$_d$, H$_e$); 3.82 (s, 3H; H$_j$), 2.84–2.79 (t, J=7.3, 2H; H$_f$), 1.60–1.52 (m, 2H; H$_g$), 1.43–1.36 (m, 2H; H$_h$) 0.87–0.82 (t, J=7.3, 3H; H$_i$). $^{13}$C NMR (75 MHz, CDCl$_3$) δ 156.98 (C$_6$), 128.56 (C$_2$), 126.54 (C$_4$), 125.22 (C$_1$), 120.98 (C$_3$), 110.28 (C$_5$), 55.73 (C$_{11}$), 31.49 (C$_7$), 30.94 (C$_8$), 22.06 (C$_9$), 13.66 (C$_{10}$). Anal. Calcd. for C$_{11}$H$_{16}$OS: C, 67.30; H, 8.22; S, 16.33; Found C, 67.43; H, 8.28; S, 16.10.

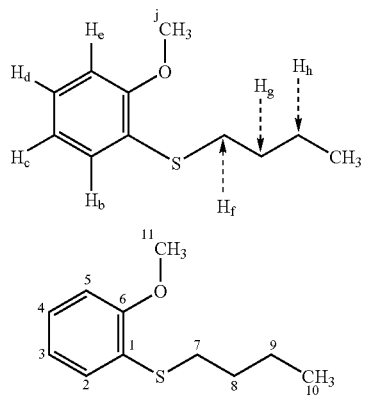

Example 3f n-Butyl 2,2'-Dimethyl-4-methylphenyl Sulfide (entry 6, Table 3): The general procedure was used to convert 2,2'-Dimethyl-4-methyl iodobenzene and n-butyl sulfide to the title product. Purification by flash chromatography (hexane as the eluent) gave the analytically pure product as a clear oil (405 mg, 98% yield). $^1$H NMR (300 MHz, CDCl$_3$) δ 6.93 (s, 2H; H$_c$, H$_{c'}$), 2.64–2.59 (t, J=7.1, 2H; H$_e$), 2.50 (s, 6H; H$_b$, H$_{b'}$), 2.26 (s, 3H; H$_d$), 1.39–1.51 (m, 4H; H$_f$, H$_g$), 0.91–0.86 (t, J=7.1, 3H; H$_h$). $^{13}$C NMR (75 MHz, CDCl$_3$) δ 142.8 (C$_5$), 137.7 (C$_3$, C$_{3'}$), 130.5 (C$_1$), 128.8 (C$_4$, C$_{4'}$), 35.2 (C$_2$, C$_{2'}$), 31.9 (C$_6$), 22.0 (C$_7$), 21.9 (C$_8$), 20.9 (C$_9$), 13.69 (C$_{10}$). Anal. Calcd. for C$_{13}$H$_{20}$S: C, 74.94; H, 9.67; S, 15.39; Found C, 74.66; H, 9.90; S, 15.32.

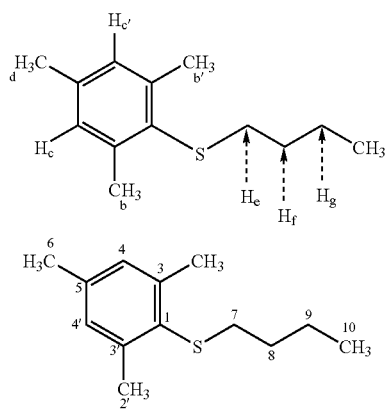

Example 3g n-Butyl 4-Iodophenyl Sulfide (entry 7, Table 3): The general procedure was used to convert diiodobenzene and n-butyl sulfide to the title product. Purification by flash chromatography (hexane as the eluent) gave the analytically pure product as a pale yellow oil (512 mg, 88% yield). $^1$H NMR (300 MHz, CDCl$_3$) δ 7.58–7.55 (d, J=8.4, 2H; H$_a$, H$_{a'}$), 7.05–7.02 (d, J=8.2, 2H; H$_b$, H$_{b'}$), 2.91–2.86 (t, J=7.3, 2H; H$_c$), 1.67–1.49 (m, 2H; H$_d$), 1.42–1.30 (m, 2H; H$_e$), 0.94–0.89 (t, J=7.3, 3H; methyl protons). $^{13}$C NMR (75 MHz, CDCl$_3$) δ 137.6 (C$_1$, C$_{1'}$), 137.2 (C$_4$), 130.2 (C$_2$, C$_{2'}$), 90.0 (C$_3$), 32.9 (C$_5$), 30.9 (C$_6$), 21.9 (C$_7$), 13.6 (C$_8$). High Resolution Mass. Spec. for C$_{10}$H$_{13}$S; Expected, 291.9783; Found, 291.9796

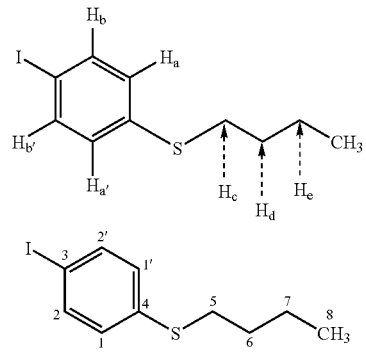

Example 3h 1,4-Bis-Butylsulfanyl-benzene (entry 8, Table 3): The general procedure was used to convert Diiodobenzene and 2 equiv. of n-butyl sulfide to the title product. Purification by flash chromatography (hexane as the eluent) gave the analytically pure product as a transparent oil (497 mg, 98% yield). $^1$H NMR (300 MHz, CDCl$_3$) δ 7.15 (d, J$_p$=0.3, 4H; H$_a$, H$_{a'}$, H$_b$, H$_{b'}$), 2.83–2.78 (t, J=7.3, 4H; H$_c$, H$_{c'}$), 1.56–1.48 (m, 4H; H$_d$, H$_{d'}$), 1.39–1.18 (m, 4H; H$_e$, H$_{e'}$), 0.86–0.81 (t, J=7.3, 6H; methyl protons). $^{13}$C NMR (75 MHz, CDCl$_3$) δ 134.2 (C$_1$, C$_{1'}$), 129.5 (C$_2$, C$_{2'}$, C$_{2''}$, C$_{2'''}$), 33.5 (C$_4$, C$_{4'}$), 31.1 (C$_5$, C$_{5'}$), 21.8 (C$_6$, C$_{6'}$), 13.5 (C$_7$, C$_{7'}$). High Resolution Mass. Spec. for C$_{14}$H$_{22}$S$_2$; Expected, 254.1163; Found, 254.1162

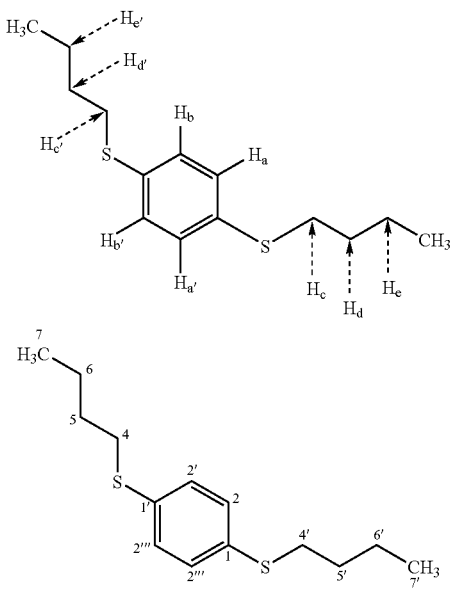

Example 3i n-Butyl 4-Bromophenyl Sulfide (entry 9, Table 3): The general procedure was used to convert 4-iodo bromobenzene and n-butyl sulfide to the title product. Purification by flash chromatography (hexane as the eluent) gave the analytically pure product as a clear oil (450 mg, 92% yield). $^1$H NMR (300 MHz, CDCl$_3$) δ 7.39–7.36 (d, J=8.6, 2H; H$_a$, H$_{a'}$), 7.19–7.15 (d, J=8.28, 2H; H$_b$, H$_{b'}$), 2.91–2.86 (t, J=7.1, 2H; H$_c$), 1.57–1.47 (m, 2H; H$_d$), 1.41–1.31 (m, 2H; H$_e$), 0.94–0.89 (t, J=7.3, 3H; H$_f$). $^{13}$C NMR (75 MHz, CDCl$_3$) δ 136.2 (C$_4$), 131.7 (C$_1$, C$_{1'}$), 130.2 (C$_2$, C$_{2'}$), 119.2 (C$_3$), 33.2 (C$_5$), 30.9 (C$_6$), 21.8 (C$_7$), 13.5 (C$_8$). Anal. Calcd. for C$_{10}$H$_{13}$Br C, 48.99; H, 5.34; S, 13.08; Found C, 49.09; H, 5.44; S, 12.96.

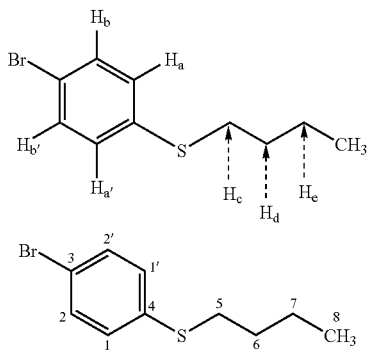

Example 3j n-Butyl 2-Naphthalene Sulfide (entry 10, Table 3): The general procedure was used to convert 2-Iodonaphthalene and n-butyl sulfide to the title product. Purification by flash chromatography (hexane) gave the analytically pure product as a clear oil (410 mg; 95% yield). $^1$H NMR (300 MHz, CDCl$_3$) δ 8.46–8.44 (d, J=8.1, 1H; H$_a$), 7.88–7.85 (d, J=7.1, 1H; H$_d$), 7.75–7.73 (d, 1H; H$_e$), 7.61–7.40 (m, 4H; H$_g$, H$_f$, H$_b$, H$_c$), 2.89–2.84 (t, 2H; H$_h$), 1.60–1.50 (m, 4H; H$_i$), 1.42–1.30 (m, 4H; H$_j$), 0.98–0.93 (t, 3H; methyl protons). $^{13}$C NMR (75 MHz, CDCl$_3$) δ 134.17 (C$_4$), 133.81 (C$_{10}$), 132.78 (C$_9$), 128.47 (C$_8$), 127.27 (C$_5$), 126.72 (C$_2$), 126.17 (C$_6$), 126.09 (C$_7$), 125.50 (C$_1$), 124.95 (C$_3$), 33.7 (C$_{11}$), 31.16 (C$_{12}$), 21.98 (C$_{13}$), 13.63 (C$_{14}$). Anal. Calcd. for C$_{14}$H$_{16}$S: C, 77.72; H, 7.45; S, 14.82; Found C, 77.44; H, 7.63; S, 14.56.

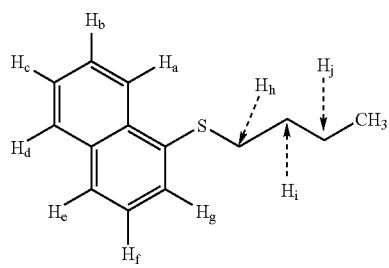

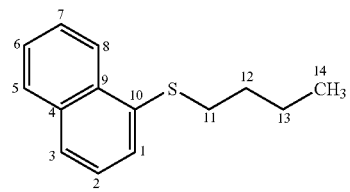

Example 3k

4-Pyrrole n-Butyl phenyl sulfide (entry 11, Table 3): The general procedure was used to convert Diiodobenzene and 2 equiv. of n-butyl sulfide to the title product. Purification by flash chromatography (hexane as the eluent) gave the analytically pure product as a white solid (430 mg, 95% yield). $^1$H NMR (300 MHz, CDCl$_3$) δ 7.45–7.37 (d, J=8.8, 2H; H$_a$, H$_{a'}$), 7.32–7.25 (d, J=8.8, 2H; H$_b$, H$_{b'}$), 7.07–7.05 (t, J=2.2, 2H; H$_g$, H$_{g'}$), 6.35–6.33 (t, J=2.07, 2H; H$_f$, H$_{f'}$), 2.95–2.90 (t, J=7.15, 2H; H$_c$), 1.59–1.52 (m, 2H; H$_d$), 1.45–1.18 (m, 2H; H$_e$), 0.95–0.90 (t, J=7.3, 3H; methyl protons). $^{13}$C NMR (75 MHz, CDCl$_3$) δ 133.8 (C$_3$), 130.5 (C$_4$), 120.8 (C$_1$, C$_{1'}$), 119.2 (C$_2$, C$_{2'}$), 118.2 (C$_8$, C$_{8'}$), 110.4 (C$_9$, C$_{9'}$), 33.9 (C$_5$), 31.1 (C$_6$), 21.9 (C$_7$), 13.5 (C$_{10}$). High Resolution Mass. Spec. for C$_{14}$H$_{17}$NS; Expected, 231.1082; Found, 231.1099.

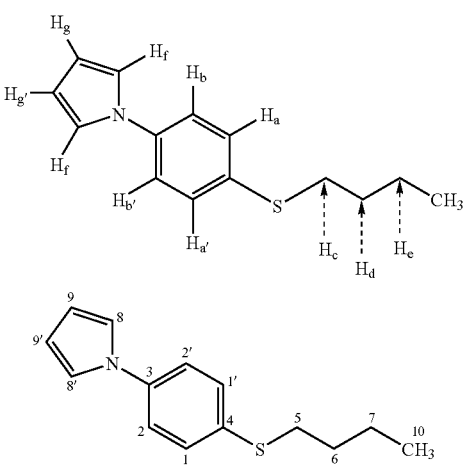

Example 3l

Cyclohexyl-phenyl sulfide (entry 12, Table 3): The general procedure was used to convert iodobenzene and cyclohexylmercaptan to the title product. Purification by flash chromatography (hexane as the eluent) gave the analytically pure product as a clear oil (297 mg, 77% yield). $^1$H NMR (300 MHz, CDCl$_3$) δ 7.44 (dd, J=6.97, 2H; H$_a$, H$_{a'}$), 7.35–7.22 (m, 3H; H$_b$, H$_{b'}$, H$_c$,), 3.19–3.11 (m, 1H; H$_d$), 2.04 (m, 2H; H$_e$, H$_i$), 1.82 (m, 2H; H$_{e'}$, H$_{i'}$), 1.65 (m, 1H; H$_g$), 1.48–1.26 (m, 5H; H$_h$, H$_f$, H$_{h'}$, H$_{f'}$, H$_{g'}$). $^{13}$C NMR (75 MHz, CDCl$_3$) δ 135.11 (C$_1$), 131.75 (C$_3$, C$_5$), 128.64 (C$_2$, C$_6$), 126.46 (C$_4$), 46.44 (C$_7$), 33.26 (C$_8$, C$_{12}$), 25.97 (C$_{10}$), 25.69 (C$_9$, C$_{11}$). Anal. Calcd. for C$_{12}$H$_{16}$S: C, 74.94; H, 8.39; S, 16.67; Found C, 75.06; H, 8.40; S, 16.54.

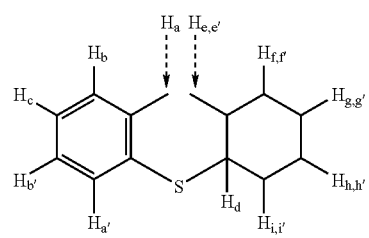

-continued

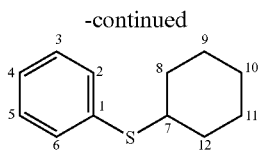

Example 4

Cu-Catalyzed Coupling of Phenyl Selenols with Aryl Iodides

General Procedure: In an argon-filled glove box, a Pyrex glass tube (2.5 cm in diameter) equipped with a Teflon stir bar, was charged with sodium tert-butoxide (Acros, 3.0 mmol), CuI (10 mol % with respect to the aryl iodide), and neocuproine (10 mol % with respect to the aryl iodide). The tube was then sealed with a rubber septum, taken out of the glove box and phenolselenol (2.2 mmol), the aryl iodide (2.00 mmol) and toluene (4.0 mL) were injected into the tube through the septum. The contents were then stirred at 110° C. for 24 hours. The reaction mixture was then cooled to room temperature and filtered to remove any insoluble residues. The filtrate was concentrated in vacuo; the residue was purified by flash column chromatography on silica gel to obtain the analytically pure product. Due to the stench and toxicity of the selenols, all glassware and syringes used were washed with bleach to reduce the odor. Phenylselenol must strictly be handled under argon at all times or the yield of the reactions is lowered and diphenyldiselenide is formed. All waste (both solid and liquid) generated from the reactions were stored in waste bottles and containers kept inside the fume hood.

Example 4a

Diphenylselenide (entry 1, Table 2): The general procedure was used to convert iodobenzene and phenylselenol to the title product. Purification by flash chromatography (hexane as the eluent) gave the analytically pure product as a clear oil (410 mg, 90% yield). $^1$H NMR (300 MHz, CDCl$_3$) δ 7.41–7.36 (m, 4H; $H_a$, $H_{a'}$, $H_d$, $H_{d'}$), 7.20–7.15 (m, 6H; $H_b$, $H_{b'}$, $H_e$, $H_{e'}$, $H_c$, $H_{c'}$). $^{13}$C NMR (75 MHz, CDCl$_3$) δ 135.70 (C$_1$), 130.94 (C$_2$), 129.10 (C$_3$), 126.94 (C$_4$). Anal. Calcd. for C$_{12}$H$_{10}$Se: C, 61.81; H, 4.32; Found C, 62.19; H, 4.38.

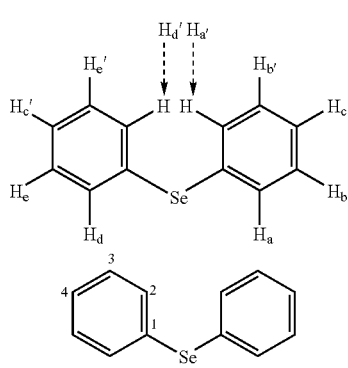

Example 4b

Phenyl-p-tolyl-selenide (entry 2, Table 2): The general procedure was used to convert 4-iodotoluene and phenylse-lenol to the title product. Purification by flash chromatography (hexane as the eluent) gave the analytically pure product as a clear oil (410 mg, 84% yield). $^1$H NMR (300 MHz, CDCl$_3$) δ 7.33–7.30 (m, 4H; $H_c$, $H_{c'}$, $H_a$, $H_{a'}$), 7.17–7.01 (m, 3H; $H_d$, $H_{d'}$, $H_e$), 7.01 (d, J=8.4, 2H; $H_b$, $H_{b'}$), 7.04 (d, J=7.9, 2H; $H_b$, $H_{b'}$), 2.23 (s, 3H; methyl protons). $^{13}$C NMR (75 MHz, CDCl$_3$) δ 137.61 (C$_{1'}$), 133.85 (C$_4$), 131.99 (C$_2$, C$_6$), 132.06 (C$_1$), 130.16 (C$_3$, C$_5$), 129.17 (C$_{2'}$, C$_{6'}$), 126.82 (C$_{3'}$, C$_{5'}$), 126.72 (C$_{4'}$), 21.12 (C$_7$). Anal. Calcd. for C$_{13}$H$_{12}$Se: C, 63.16; H, 4.89; Found C, 63.29; H, 5.07.

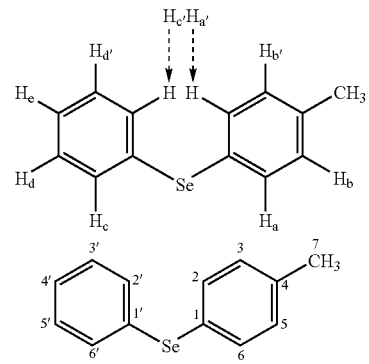

Example 4c

Phenyl-o-tolyl-selenide (entry 3, Table 2): The general procedure was used to convert 2-iodotoluene and phenylse-lenol to the title product. Purification by flash chromatography (hexane as the eluent) gave the analytically pure product as a pale yellow oil (386 mg, 80% yield). $^1$H NMR (300 MHz, CDCl$_3$) δ 7.30–6.94 (m, 9H; $H_a$, $H_b$, $H_c$, $H_d$, $H_e$, $H_{e'}$, $H_f$, $H_{f'}$, $H_g$), 2.29 (s, 3H; methyl protons). $^{13}$C NMR (75 MHz, CDCl$_3$) δ 139.75 (C$_8$), 133.56 (C$_6$), 132.68 (C$_1$), 130.67 (C$_2$), 130.17 (C$_5$), 129.30 (C$_9$, C$_{13}$), 127.70, (C$_{10}$, C$_{12}$), 127.07 (C$_3$), 126.66 (C$_{11}$), 126.27 (C$_4$), 20.30 (C$_7$). Anal. Calcd. for C$_{13}$H$_{12}$Se: C, 63.16; H, 4.89; Found C, 63.23; H, 5.14.

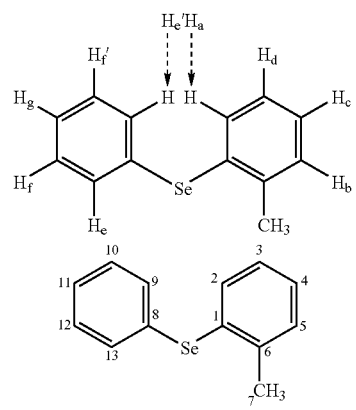

Example 4e

1-Methoxy-4-phenylselanyl-benzene (entry 4, Table 2): The general procedure was used to convert 4-iodoanisole and phenylselenol to the title product. Purification by flash chromatography (hexane/CH$_2$Cl$_2$ [4:1] as the eluent) gave the analytically pure product as a clear oil (460 mg, 88% yield). $^1$H NMR (300 MHz, CDCl$_3$) δ 7.42 (d, J=8.8, 2H; H$_a$, H$_{a'}$), 7.25–7.09 (m, 5H; H$_c$, H$_{c'}$, H$_d$, H$_{d'}$, H$_e$), 6.76 (d, J=8.8, 2H; H$_b$, H$_{b'}$), 3.70 (s, 3H; methyl protons). $^{13}$C NMR (75 MHz, CDCl$_3$) δ 159.7 (C$_4$), 136.5 (C$_8$), 133.1 (C$_2$, C$_6$), 130.8 (C$_9$, C$_{13}$), 129.1 (C$_{10}$, C$_{12}$), 126.3 (C$_{11}$), 119.8 (C$_1$), 115.1 (C$_3$, C$_5$), 55.23 (C$_7$). Anal. Calcd. for C$_{13}$H$_{12}$OSe: C, 59.32; H, 4.60; Found C, 59.44; H, 4.61.

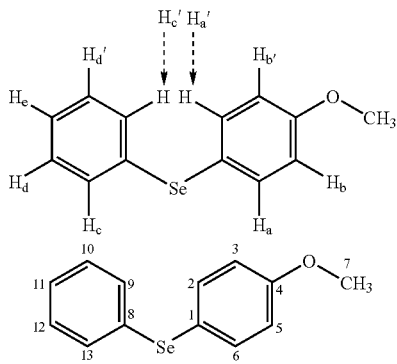

Example 4f

1-Methoxy-2-phenylselanyl-benzene (entry 5, Table 2): The general procedure was used to convert 2-iodoanisole and phenylselenol to the title product. Purification by flash chromatography (hexane/CH$_2$Cl$_2$ [4:1] as the eluent) gave the analytically pure product as a clear oil (430 mg, 78% yield). $^1$H NMR (300 MHz, CDC$_{13}$) δ 7.50–7.05 (m, 6H; H$_c$, H$_e$, H$_{e'}$, H$_f$, H$_{f'}$, H$_g$) 7.12 (dd, J=7.5, 1H; H$_a$), 6.75–6.65 (m, 2H; H$_b$, H$_d$), 3.76 (s, 3H; methyl protons). $^{13}$C NMR (75 MHz, CDCl$_3$) δ 156.48 (C$_6$), 135.34 (C$_8$), 130.65 (C$_2$), 129.35 (C$_9$, C$_{13}$), 128.13 (C$_{10}$, C$_{12}$), 128.01 (C$_4$), 127.61 (C$_{11}$), 121.80 (C$_1$), 121.52 (C$_3$), 110.28 (C$_5$), 55.75 (C$_7$). Anal. Calcd. for C$_{13}$H$_{12}$OSe: C, 59.32; H, 4.60; Found C, 59.28; H, 4.65.

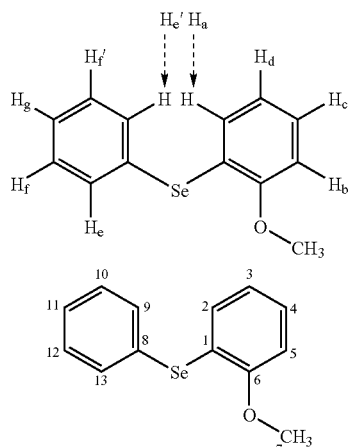

Example 4g 4-n-Butylselanyl-benzene (entry 6, Table 2): The general procedure was used to convert 4-n-butyl-iodobenzene and phenylselenol to the title product. Purification by flash chromatography (hexane as the eluent) gave the analytically pure product as a transparent oil (520 mg, 90% yield). $^1$H NMR (300 MHz, CDCl$_3$) δ 7.35–7.31 (m, 4H; H$_a$, H$_{a'}$, H$_b$, H$_{b'}$), 7.18–7.13 (m, 3H; H$_h$, H$_{h'}$, H$_i$), 7.03–6.99 (m, 2H; H$_g$, H$_{g'}$), 2.53 (t, 2H; H$_c$), 1.53–1.18 (m, 4H; H$_d$, H$_e$), 0.87 (t, 3H; H$_f$). $^{13}$C NMR (75 MHz, CDCl$_3$) δ 142.56 (C$_4$), 133.65 (C$_9$), 132.14 (C$_2$, C$_{2'}$), 131.93 (C$_1$), 129.49 (C$_3$, C$_{3'}$), 129.17 (C$_{11}$, C$_{10'}$), 127 (C$_{11}$, C$_{11'}$), 126.86 (C$_{12}$), 32.25 (C$_5$), 33.46 (C$_6$), 22.31 (C$_7$), 13.92 (C$_8$). Anal. Calcd. for C$_{16}$H$_{18}$Se: C, 66.43; H, 6.27; Found C, 66.68; H, 6.54.

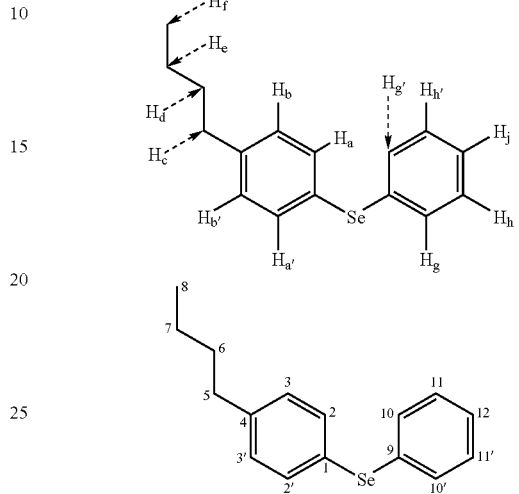

Example 4h (2,4,6-trimethyl-phenyl)-phenyl selenide (entry 7, Table 2): The general procedure was used to convert 2,4,6-trimethyliodobenzene and phenylselenol to the title product. Purification by flash chromatography (hexane as the eluent) gave the analytically pure product as a clear oil (451 mg, 82% yield). $^1$H NMR (300 MHz, CDCl$_3$) δ 6.82 (s, 2H; H$_a$, H$_{a'}$), 6.96–6.87 (m, 3H; H$_c$, H$_{c'}$, H$_d$, H$_b$, H$_{b'}$) 2.26 (s, 6H; ortho methyl protons), 2.13 (s, 3H, para methyl protons). $^{13}$C NMR (75 MHz, CDCl$_3$) δ 144.06 (C$_2$, C$_6$), 139.51 (C$_4$), 133.87 (C$_1$), 129.53 (C$_{10}$), 129.27 (C$_{11}$, C$_{15}$), 128.82 (Cl$_2$, C$_{14}$), 127.15 (C$_3$, C$_5$), 125.76 (C$_{13}$), 24.70 (C$_7$, C$_8$), 21.49 (C$_9$). Anal. Calcd. for C$_{15}$H$_{16}$Se: C, 65.45; H, 5.86; Found C, 65.31; H, 5.86.

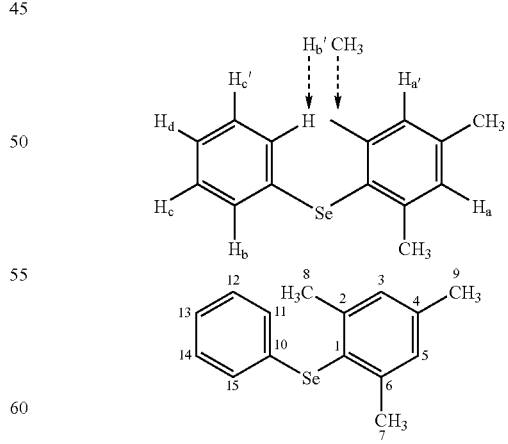

Example 4i 2-phenylselanyl-thiophene (entry 8, Table 2): The general procedure was used to convert 2-iodophenol and phenylselenol to the title product. Purification by flash chromatography (hexane as the eluent) gave the analytically pure product as a pale yellow oil (320 mg, 68% yield). $^{1}$H NMR (300 MHz, CDCl$_3$) δ 7.37 (dd, J=6.5, 1H; H$_f$), 7.26–7.23 (m, 3H; H$_a$, H$_{a'}$, H$_e$), 7.16–7.11 (m, 3H; H$_b$, H$_{b'}$, H$_c$), 6.98–6.94 (dd, J=8,85, 1H; H$_d$). $^{13}$C NMR (75 MHz, CDCl$_3$) δ 137.02 (C$_1$), 133.39 (C$_7$), 132.05 (C$_9$), 129.84 (C$_2$, C$_6$), 129.18 (C$_3$, C$_5$), 129.84 (C$_8$), 128.30 (C$_{10}$), 126.68 (C$_4$). Anal. Calcd. for C$_{10}$H$_8$SSe: C, 50.21; H, 3.37; S, 13.41; Found C, 50.37; H, 3.37; S, 13.62.

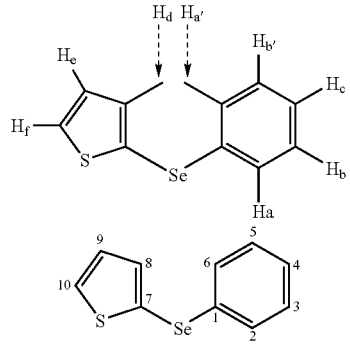

Example 4i 1-phenylselanyl-naphthalene (entry 9, Table 2): The general procedure was used to convert 2-iodonaphthalene and phenylselenol to the title product. Purification by flash chromatography (hexane) gave the analytically pure product as a clear oil (400 mg, 72% yield). $^{1}$H NMR (300 MHz, CDCl$_3$) δ 8.25–8.22 (m, 1H; H$_a$), 7.74–7.64 (m, 3H; H$_e$, H$_f$, H$_g$), 7.42–7.36 (m, 2H; H$_g$, H$_{g'}$), 7.27–7.21 (m, 3H; H$_b$, H$_c$, H$_d$), 7.24–7.21 (m, 3H; H$_h$, H$_{h'}$, H$_j$). $^{13}$C NMR (75 MHz, CDCl$_3$) δ 134.06 (C$_4$), 134.03 (C$_9$), 133.79 (C$_{10}$), 131.66 (C$_3$), 131.61 (C$_8$), 129.31 (C$_5$), 129.24 (C$_6$), 129.14 (C$_7$), 128.53 (C$_1$), 127.59 (C$_2$), 126.89 (C$_{11}$), 126.75 (C$_{12}$, C$_{12'}$), 126.31 (C$_{13}$, C$_{13'}$), 125.97 (C$_{14}$). Anal. Calcd. for C$_{16}$H$_{12}$Se: C, 67.85; H, 4.27; Found C, 67.72; H, 4.24.

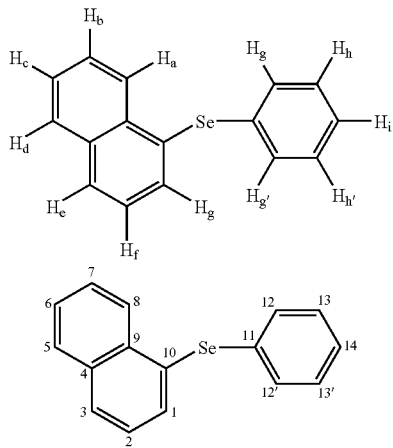

Example 4k

4-Pyrrole 1-selanylbenzene (entry 10, Table 2): The general procedure was used to convert 1-(4-iodophenyl)pyrrole and phenylselenol to the title product. Purification by flash chromatography (hexane as the eluent) gave the analytically pure product as a white solid (450 mg, 76% yield). $^{1}$H NMR (300 MHz, CDCl$_3$) δ 7.48–7.38 (m, 3H; H$_d$, H$_g$, H$_{d'}$), 7.26–7.19 (m, 6H; H$_b$, H$_{b'}$, H$_a$, H$_{a'}$, H$_c$, H$_{c'}$), 7.07 (t, J=4.3, 2H; H$_e$, H$_{e'}$), 6.28 (t, J=4.3, 2H; H$_f$, H$_{f'}$). $^{13}$C NMR (75 MHz, CDCl$_3$) δ 134.54 (C$_3$), 133.35 (C$_{10}$), 132.68 (C$_1$, C$_{1'}$), 131.85 (C$_2$, C$_{2'}$), 129.40 (C$_8$, C$_{8'}$), 127.38 (C$_9$, C$_{9'}$), 125 (C$_7$), 121.16 (C$_4$), 119.13 (C$_5$, C$_{5'}$), 110.70 (C$_6$, C$_{6'}$). Anal. Calcd. for C$_{16}$H$_{13}$NSe: C, 64.43; H, 4.39; Found C, 64.35; H, 4.56. Melting Point: 86–88° C.

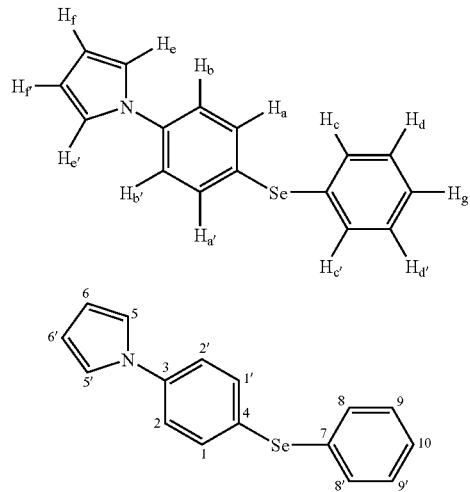

Example 4l 1,2-bis(phenylseleno)benzene (entry 11, Table 2): The general procedure was used to convert 1,2-diiodo-benzene and 2.2 equiv. of phenylselenol to the title product. Purification by flash chromatography (hexane as the eluent) gave the analytically pure product as a transparent oil (310 mg, 81% yield). $^{1}$H NMR (300 MHz, CDCl$_3$) δ 7.45–7.40 (m, 4H; H$_a$, H$_{a'}$), 7.23–7.20 (m, 6H; H$_b$, H$_{b'}$, H$_c$, H$_{c'}$), 7.12–7.09 (m, 2H; H$_d$, H$_{d'}$), 6.99–6.94 (m, 2H; H$_e$, H$_{e'}$). $^{13}$C NMR (75 MHz, CDCl$_3$) δ 135.80 (C$_1$), 133.90 (C$_2$, C$_{2'}$), 132.90 (C$_6$, C$_{6'}$), 130.55 (C$_5$, C$_{5'}$), 129.48 (C$_3$, C$_{3'}$) 127.87 (C$_4$, C$_{4'}$), 127.82 (C$_7$, C$_{7'}$) Anal. Calcd. for C$_{18}$H$_{14}$Se$_2$: C, 55.69; H, 3.63; Found C, 55.50; H, 3.62.

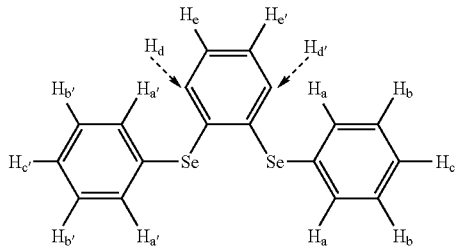

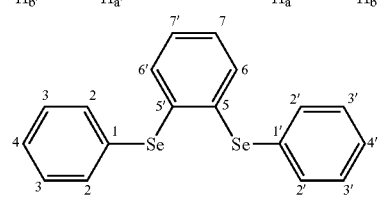

Example 4m 2-aniline-phenyl-phenyl selenide (entry 12, Table 2): The general procedure was used to convert 2-iodoaniline and phenylselenol to the title product. Purification by flash chromatography (hexane/dichloromethane [4:1] as the eluent) gave the analytically pure product as a white solid (300 mg, 62% yield). $^1$H NMR (300 MHz, CDCl$_3$) δ 7.50 (dd, J=7.7, H; Ha), 7.16–7.08 (m, 6H; H$_g$, H$_f$ H$_{f'}$, H$_e$, H$_{e'}$, H$_d$), 6.75 (dd, J=7.9, 1H; H$_c$), 6.63 (dd, J=7.5, 1H; H$_a$) $^{13}$C NMR (75 MHz, CDCl$_3$) δ 147.9 (C$_6$), 138.4 (C$_1$), 131.5 (C$_3$), 130.9 (C$_4$), 129.4 (C$_9$, C$_{9'}$), 129.2 (C$_8$, C$_{8'}$), 126.1 (C$_2$), 119.1 (C$_5$), 115.3 (C$_{10}$), 113.1 (C$_7$). Anal. Calcd. for C$_{12}$H$_{11}$NSe: C, 58.07; H, 4.47, N, 5.64. Found C, 58.35; H, 4.61; N, 5.53.

Example 5b 2-nitro-phenyl-phenyl selenide (entry 2, Table 3): The general procedure was used to convert 2-nitro iodobenzene and phenylselenol to the title product. Purification by flash chromatography (hexane/dichloromethane [4:1] as the eluent) gave the analytically pure product as a white solid (450 mg, 81% yield). $^1$H NMR (300 MHz, CDCl$_3$) δ 8.22 (dd, J=7.5, H; Ha), 7.62 (d, J=6.5, 2H; H$_b$, H$_c$), 7.45–7.35 (m, 3H; H$_f$, H$_{f'}$, H$_g$), 7.24–7.15 (m, 2H; H$_e$, H$_{e'}$), 6.92 (d, J=7.53, 1H; H$_d$). $^{13}$C NMR (75 MHz, CDCl$_3$) δ 145.9 (C$_6$), 137.3 (C$_8$, C$_{8'}$), 135.8 (C$_3$), 133.6 (C$_1$), 130.1 (C$_9$, C$_{9'}$), 130 (C$_4$), 129.8 (C$_5$), 128 (C$_{10}$), 126 (C$_2$), 125.7 (C$_7$). Anal. Calcd. for C$_{12}$H$_9$NO$_2$Se: C, 51.81; H, 3.26, N, 5.04. Found C, 51.96; H, 3.38; N, 4.98.

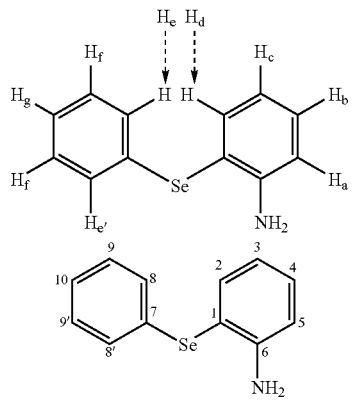

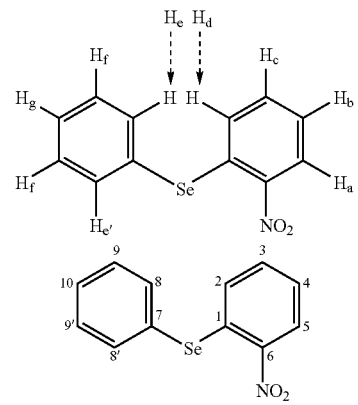

Example 5a 4-nitro-phenyl-phenyl selenide (entry 1, Table 3): The general procedure was used to convert 4-nitro iodobenzene and phenylselenol to the title product. Purification by flash chromatography (hexane/dichloromethane [4:1] as the eluent) gave the analytically pure product as a white solid (290 mg, 75% yield). $^1$H NMR (300 MHz, CDCl$_3$) δ 8.02 (dd, J=8.4, 2H; H$_b$, H$_{b'}$), 7.63 (dd, J=8.1, 2H; H$_a$, H$_{a'}$), 7.45–7.25 (m, 5H; H$_d$, H$_{d'}$, H$_e$, H$_c$, H$_{c'}$). $^{13}$C NMR (75 MHz, CDCl$_3$) δ 137.6 (C$_4$), 134.8 (C$_3$, C$_{3'}$), 129 (C$_2$, C$_{2'}$), 128.6 (C$_6$, C$_{6'}$), 128.3 (C$_7$, C$_{7'}$), 126.1 (C$_1$), 130.1 (C$_5$), 128.4 (C$_8$). Anal. Calcd. for C$_{12}$H$_9$NO$_2$Se: C, 51.81; H, 3.26; N, 5.04. Found C, 52.05; H, 3.34; N, 4.88.

Example 5c

Methyl p-(phenylseleno)benzoate (entry 3, Table 3): The general procedure was used to convert methyl-4-iodobenzoate and phenylselenol to the title product. Purification by flash chromatography (hexane/dichloromethane [3:2] as the eluent) gave the analytically pure product as a white solid (481 mg, 84% yield). $^1$H NMR (300 MHz, CDCl$_3$) δ 7.88 (d, J=8.2, 2H; H$_b$, H$_{b'}$), 7.59–7.56 (m, 2H; H$_a$, H$_{a'}$), 7.38–7.35 (m, 5H; H$_d$, H$_{d'}$, H$_e$, H$_c$, H$_{c'}$), 3.88 (s, 3H; methyl protons). $^{13}$C NMR (75 MHz, CDCl$_3$) δ 166.7 (C$_{13}$), 136.1 (C$_1$), 135.9 (C$_4$), 134.9 (C$_8$, C$_{12}$), 129.6 (C$_7$), 130.3 (C$_9$, C$_{11}$), 130.1 (C$_3$, C$_5$), 128.4 (C$_{10}$), 128.1 (C$_2$, C$_6$), 52.5 (C$_{14}$). Anal. Calcd. for C$_{14}$H$_{12}$O$_2$Se: C, 57.74; H, 4.15; Found C, 57.92; H, 4.39. Melting Point; 79–80° C.

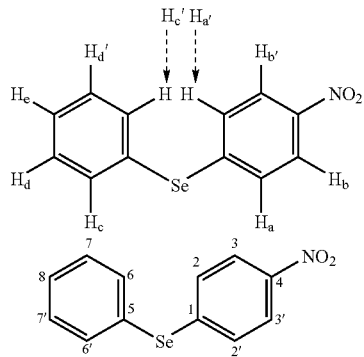

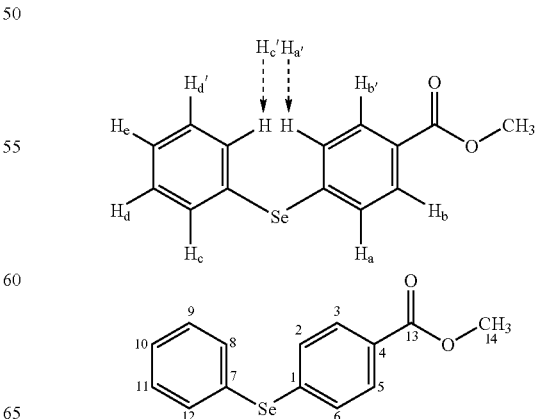

Example 5d

Methyl o-(phenylseleno)benzoate (entry 4, Table 3): The general procedure was used to convert methyl-2-iodobenzoate and phenylselenol to the title product. Purification by flash chromatography (hexane/dichloromethane[3:2] as the eluent) gave the analytically pure product as a clear oil (401 mg, 76% yield). $^1$H NMR (300 MHz, CDCl$_3$) δ 7.88 (dd, J=6.22, 1H; H$_d$), 7.47 (m, 2H; H$_a$, H$_b$), 7.33 (m, 3H; H$_e$, H$_{e'}$, H$_{f'}$), 7.14 (td, J=5.4, 1H; H$_c$), 7.04 (td, J=6.02, 1H; H$_f$), 6.73 (dd, J=6.7, 1H; H$_g$), 3.85 (s, 3H; methyl protons). $^{13}$C NMR (75 MHz, CDCl$_3$) δ 166.79 (C$_{13}$), 143.15 (C$_1$), 135.47 (C$_6$), 132.39 (C$_3$), 132.22 (C$_2$), 130.93 (C$_5$), 129.65 (C$_7$), 129.02 (C$_8$, C$_{12}$), 127.28 (C$_9$, C$_{11}$), 126.58 (C$_{10}$), 124.19 (C$_4$), 52.10 (C$_{14}$). Anal. Calcd. for C$_{14}$H$_{12}$O$_2$Se: C, 57.74; H, 4.15; Found C, 57.85; H, 4.31.

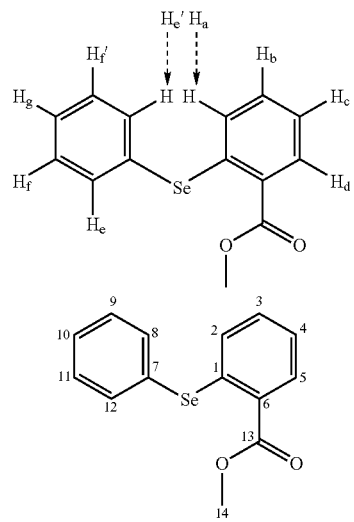

Example 5e 4-fluoro-phenyl-phenyl selenide (entry 5, Table 3): The general procedure was used to convert 2-nitro iodobenzene and phenylselenol to the title product. Purification by flash chromatography (hexane/dichloromethane [4:1] as the eluent) gave the analytically pure product as a white solid (460 mg, 92% yield). $^1$H NMR (300 MHz, CDCl$_3$) δ 7.14–7.27 (m, 4H; H$_a$, H$_{a'}$, H$_b$, H$_{b'}$), 7.16–7.13 (m, 3H; H$_d$, H$_e$, H$_{d'}$), 6.87 (dd, J=8.6, 2H; H$_c$, H$_{c'}$). $^{13}$C NMR (75 MHz, CDCl$_3$) δ 160.8 (C$_4$), 135.7 (C$_2$, C$_{2'}$), 135.6 (C$_3$, C$_{3'}$), 132.1 (C$_6$, C$_{6'}$), 129.3 (C$_1$), 127.1 (C$_5$), 116.6 (C$_7$, C$_{7'}$), 116.3 (C$_8$). Anal. Calcd. for C$_{12}$H$_9$FSe: C, 57.39; H, 3.61. Found C, 57.54; H, 3.65.

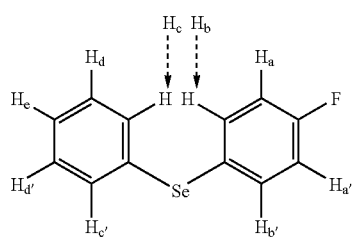

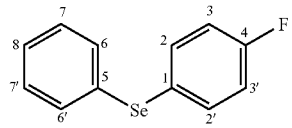

Example 5f 4-aceto-phenyl-phenyl selenide (entry 6, Table 3): The general procedure was used to convert 4-iodo-acetophenone and phenylselenol to the title product. Purification by flash chromatography (hexane/dichloromethane [4:1] as the eluent) gave the analytically pure product as a white solid (420 mg, 78% yield). $^1$H NMR (300 MHz, CDCl$_3$) δ 7.79 (dd, J=8.2, 2H; H$_b$, H$_{b'}$), 7.59 (dd, J=7.7, 2H; H$_a$, H$_{a'}$), 7.38–7.35 (m, 5H; H$_d$, H$_{d'}$, H$_e$, H$_c$, H$_{c'}$). $^{13}$C NMR (75 MHz, CDCl$_3$) δ 197.7 (C$_9$), 140.7 (C$_4$), 135.5 (C$_2$, C$_{2'}$), 134.1 (C$_5$), 130.6 (C$_3$, C$_{3'}$), 130.1 (C$_7$, C$_{7'}$), 129.3 (C$_1$), 129 (C$_6$, C$_{6'}$), 128.8 (C$_8$), 26.8 (C$_{10}$). Anal. Calcd. for C$_{14}$H$_{12}$OSe: C, 61.10; H, 4.40. Found C, 61.38; H, 4.63.

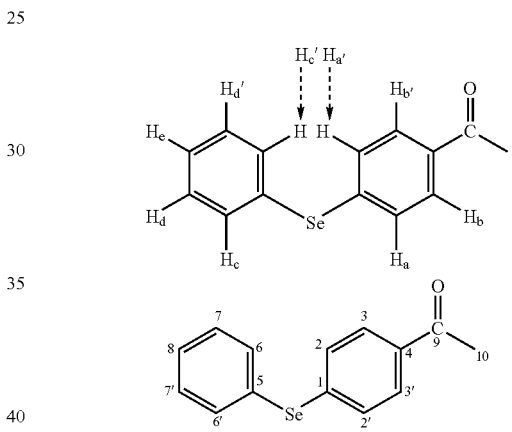

Example 6

The general synthetic procedures relating to the compounds of the preceding examples can be modified by way of choice and amount of copper(I) halide, ligand, base and/or solvent utilized, with corresponding modification in preparation of the metal-ligand catalyst complex/compounds. For instance, the aforementioned Cu(phen)(PPh$_3$)Br and Cu(neocup)(PPh$_3$)Br compounds can be prepared by addition of 1,10-phenanthroline or neocuproine, respectively, to a solution of tris(triphenylphospine)copper(I) bromide in chloroform. Such preparations are known in literature. See, Gujadhur, R. K.; Bates, C. G.; Venkataraman, D. Org. Lett. 2001, 3, 4315–4317, and the supporting information referenced therein. Depending on choice of ligand, aryl halide and/or thiol or selenol, other useful solvents include dichloromethane, toluene, benzene, NMP, DMF and DMSO. Likewise, the ligands of such catalyst compounds can alternatively comprise components represented by the structures of FIG. 2. The precursors for such components would be known in the art, as would modification in preparation of the corresponding catalyst and resulting aryl-sulfur or aryl-selenium product—such modification as can further include choice of base to effect the desired reaction.

Example 7a

Cu-catalyzed coupling of thiols with vinyl halides. In an argon-filled glove box, a Pyrex glass tube (2.5 cm in diameter) equipped with a Teflon-coated stir bar, was charged with a base and copper catalyst, as described herein. The tube was then sealed with a rubber septum, taken out of the glove box and solvent (4.0 mL) and 1.00 mmol of a thiol and 1.00 mmol of a vinyl iodide were injected into the tube through the septum, with the thiol and vinyl iodide chosen for a particular desired vinyl sulfide. The contents were then stirred at 70–110° C. (depending on the solvent) for up to 24 hours. The reaction mixture was then cooled to room temperature and filtered through a pad of celite to remove any insoluble residues. The filtrate was concentrated in vacuo; the residue was purified by flash column chromatography on silica gel to obtain the analytically pure vinyl sulfide product.

Example 7b

The methodology of Example 7a was used with various combinations of known Cu(I) compounds, bases and solvents, as provided in Table 7, for the cross-coupling of (E)-1-iodooctene and thiophenol. Without limitation, the method of Example 7a (and reagents of Table 7) can also be used to couple any thiol/vinyl halide combination available by way of the compounds and structures of FIGS. 3A–D.

TABLE 7

| Solvent | Copper Catalyst* | Base |
| --- | --- | --- |
| THF | Cu(phen)(PPh$_3$)$_2$NO$_3$ | CsOAc |
| Dioxane | Cu(phen)PPh$_3$Br | DBU |
| Isopropyl alcohol | Cu(neocup)PPh$_3$Cl | K$_3$PO$_4$ |
| Toluene | CuI/neocuproine | Na$_2$CO$_3$ |
|  | Cu(neocup)PPh$_3$I | NaOtBu |
|  | Cu(neocup)PPh$_3$Br | K$_2$CO$_3$ |
|  | CuI/neocuproine | Cs$_2$CO$_3$ |
|  | CuCl/Phen | NaOtBu |
|  | Cu(bipy)PPh$_3$Br | KOtBu |
|  | [Cu(CH$_3$CN)]PF$_6$ |  |
|  | Cu(PPh$_3$)$_3$Br |  |

*Phen = 1,10-phenanthroline; neocup = 2,9-dimethyl-1,10-phenathroline (neocuproine); bipy = 2,2'-bipyridine Various other Cu(I) compounds useful in the synthesis of vinyl sulfides can be prepared as would be understood in the art with reference to Example 6 and the bi-dentate ligands of FIG. 2.

While the principles of this invention have been described in connection with specific embodiments, it should be understood clearly that these descriptions are added only by way of example and are not intended to limit, in any way, the scope of this invention. For instance, vinyl halides, including those provided in FIG. 3D, can be coupled using the present methodologies with various selenol compounds of the sort which can otherwise be used for coupling with aryl halides. As with the vinyl sulfides prepared using this invention, the range of vinyl selenides is limited only by the commercial or synthetic availability of the corresponding selenide and vinyl halide, in conjunction with a Cu(I) metal-ligand compound and/or base component, either of which can be selected without undue experimentation and used according to procedures of the sort described herein, as would be understood by those skilled in the art.

We claim:

1. A method of using a Cu(I) compound for aryl-sulfur and aryl-selenide bond formation, said method comprising:
   providing an aryl halide, and one of a thiol and a selenol; and
   contacting said halide and one of said thiol and said selenol with a Cu(I) compound selected from a Cu(I) salt, a bi-dentate ligand, and the reaction product of said Cu(I) salt and said bi-dentate ligand.

2. The method of claim 1 wherein said Cu(I) compound is in an amount less than stoichiometric.

3. The method of claim 2 wherein said bi-dentate ligand is selected from 1,10-phenanthroline and 2,9-dimethyl-1,10-phenanthroline.

4. The method of claim 3 wherein said Cu(I) compound comprises a Cu(I) halide and one of said bi-dentate ligands.

5. The method of claim 1 further comprising a base component.

6. The method of claim 1 wherein said thiol is selected from aryl and alkyl thiols, and said selenol is selected from aryl and alkyl selenols.

7. A system for aryl-sulfur and aryl-selenide bond formation, said system comprising:
   an aryl halide;
   a compound selected from a thiol, said thiol selected from aryl and alkyl thiols, and a selenol, said selenol selected from aryl and alkyl selenols; and
   a Cu(I) compound selected from a Cu(I) salt, a bi-dentate ligand, and a reaction product of said Cu(I) salt and said bi-dentate ligand, said Cu(I) compound present in an amount less than stoichiometric.

8. The system of claim 7 comprising a catalytic amount of said Cu(I) compound.

9. The system of claim 7 wherein said bi-dentate ligand is selected from 1,10-phenanthroline and 2,9-dimethyl-1,10-phenanthroline.

10. The system of claim 9 wherein said Cu(I) compound comprises a chelation product of a Cu(I) halide and one of said bi-dentate ligands.

11. The system of claim 7 further comprising a solvent.

12. The system of claim 7 further comprising a base component.

13. A method for coupling halides and thiols, said method comprising:
   providing an enyl halide compound, said enyl halide compound selected from aryl halides and vinyl halides;
   providing a thiol compound, said thiol compound selected from alkyl thiols, aryl thiols and heterocyclic thiols; and
   contacting said halide and thiol compounds with a medium comprising a Cu(I) compound selected from a Cu(I) salt, a bi-dentate ligand, and a reaction product of said Cu(I) salt and said bi-dentate ligand, said Cu(I) compound in an amount less than stoichiometric, and said medium further comprising a solvent component.

14. The method of claim 13 wherein said enyl halide is a vinyl halide selected from cyclic and acyclic vinyl iodides.

15. The method of claim 13 wherein said thiol is a thiophenol.

16. The method of claim 13 wherein said bi-dentate ligand is selected from 1,10-phenanthroline and 2,9-dimethyl-1,10-phenanthroline.

17. The method of claim 16 wherein said Cu(I) compound is selected from Cu(phen)(PPh$_3$)$_2$NO$_3$ and CuI/neocuproine.

18. The method of claim 17 wherein said solvent is selected from toluene and isopropyl alcohol.

19. The method of claim 18 wherein said medium further comprises a base component.

20. The method of claim 19 wherein said base component is K$_3$PO$_4$.

* * * * *

UNITED STATES PATENT AND TRADEMARK OFFICE
CERTIFICATE OF CORRECTION

PATENT NO. : 7,112,697 B1
APPLICATION NO. : 10/889311
DATED : September 26, 2006
INVENTOR(S) : Dhandapani Venkataraman, Craig G. Bates and Rattan K. Gujadhur It is certified that error appears in the above-identified patent and that said Letters Patent is hereby corrected as shown below:

Col. 14, Line 21: "transesterifcation" should be -- transesterification--

Col. 18, Line 59: "Cu cat. = [Cu(phen)PPh$_3$)$_2$]NO3 or CuI/Neocuproine" should be
-- Cu cat. = [Cu(phen)(PPh$_3$)$_2$]NO3 or CuI/Neocuproine --

Col. 34, Lines 9-10: "$H_a H_a$" should be -- $H_a H_{a'}$ --

Col. 35, Line 38: "(entry 1, Table 2)" should be --(entry 1, Table 5) --

Col. 36, Line 31: "(entry 3, Table 2)" should be -- (entry 3, Table 5) --

Col. 36, Line 65: "(entry 4, Table 2)" should be -- (entry 4, Table 5) --

Col. 37, Line 28: "(entry 5, Table 2)" should be -- (entry 5, Table 5) --

Col. 37, Line 63: "(entry 6, Table 2)" should be -- (entry 6, Table 5) --

Col. 38, Line 32-33: "(entry 7, Table 2)" should be -- (entry 7, Table 5) --

Col. 38, Line 66: "(entry 8, Table 2)" should be -- (entry 8, Table 5) --

Col. 39, Line 29: "(entry 9, Table 2)" should be -- (entry 9, Table 5) --

Col. 39, Line 62: "4-Pyrrole 1-selanylbenzene" should be -- 4-Pyrrole 1-(phenylselanyl) benzene--

Col. 39, Line 63: "(entry 10, Table 2)" should read --(entry 10, Table 5) --

Col. 40, Line 35: "(entry 11, Table 2)" should read --(entry 11, Table 5) --

Col. 41, Line 3: "2-aniline-phenyl-phenyl selenide" should be -- 2-(phenylselenyl)-aniline--

Col. 41, Line 3: "(entry 12, Table 2)" should read -- (entry 12, Table 5) --

Col. 41, Line 39: "(entry 1, Table 3)" should read -- (entry 1, Table 6) --

Col. 42, Line 3: "(entry 2, Table 3)" should read -- (entry 2, Table 6) --

Col. 42, Line 37: "(entry 3, Table 3)" should read -- (entry 3, Table 6) --

UNITED STATES PATENT AND TRADEMARK OFFICE
CERTIFICATE OF CORRECTION

PATENT NO. : 7,112,697 B1
APPLICATION NO. : 10/889311
DATED : September 26, 2006
INVENTOR(S) : Dhandapani Venkataraman, Craig G. Bates and Rattan K. Gujadhur It is certified that error appears in the above-identified patent and that said Letters Patent is hereby corrected as shown below:

Col. 43, Line 3: "(entry 4, Table 3)" should read -- (entry 4 Table 6) --

Col. 43, Line 44: "(entry 5, Table 3)" should read -- (entry 5, Table 6) --

Col. 44, Line 13: "(entry 6, Table 3)" should read -- (entry 6, Table 6) --

Signed and Sealed this

Seventh Day of August, 2007

JON W. DUDAS
*Director of the United States Patent and Trademark Office*

UNITED STATES PATENT AND TRADEMARK OFFICE
CERTIFICATE OF CORRECTION

PATENT NO. : 7,112,697 B1
APPLICATION NO. : 10/889311
DATED : September 26, 2006
INVENTOR(S) : Dhandapani Venkataraman et al.

It is certified that error appears in the above-identified patent and that said Letters Patent is hereby corrected as shown below:

Col. 18, Line 53, "/PrOH" should be --iPrOH--

Col. 25, Line 32: "$C_3$'" should be --$C_{3'}$--

Col. 25, Line 32: "$C_2, _{C6'}$" should be --$C_{2'}, C_{6'}$--

Col. 26, Line 28: "HC" should be --$H_c$--

Col. 28, Line 3: "$H_c, H_{c''}$" should be --$H_c, H_{c'}$--

Col. 28, Line 7: "$C_1$" should be --$C_{11}$--

Col. 28, Line 65: "$C_3$'" should be --$C_{3'}$--

Col. 28, Line 65: "$C_2, C_2$" should be --$C_2, C_{2'}$--

Col. 29, Line 31: "$C_2, C_2$" should be --$C_2, C_{2'}$--

Col. 30, Line 30: "$C_2, C_2$" should be --$C_2, C_{2'}$--

Col. 30, Line 31: "$C_3, C_3$" should be --$C_3, C_{3'}$--

Col. 30, Line 66: "$C_{11}H_{160}S: C, 67.30;$" should be --$C_{11}H_{16}OS: C, 67.30$--

Col. 32, Line 59: "2''''" should be --2''''--
Example 3h drawings should appear as follows:

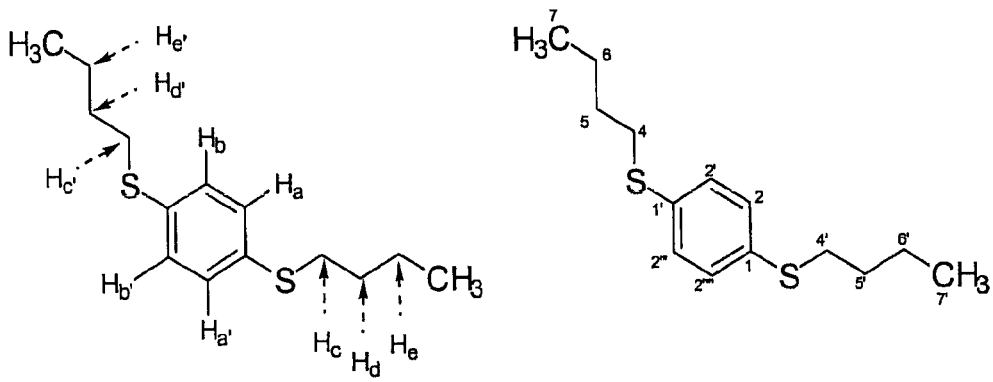

Col. 34, Line 16: "$C_2, C_2$" should be --$C_2, C_{2'}$--

UNITED STATES PATENT AND TRADEMARK OFFICE
CERTIFICATE OF CORRECTION

PATENT NO.       : 7,112,697 B1
APPLICATION NO.  : 10/889311
DATED            : September 26, 2006
INVENTOR(S)      : Dhandapani Venkataraman et al.

Page 2 of 3

It is certified that error appears in the above-identified patent and that said Letters Patent is hereby corrected as shown below:

Col. 34, Line 26: "$H_f$" should be --$H_{f'}$--
Example 3k drawings should appear as follows:

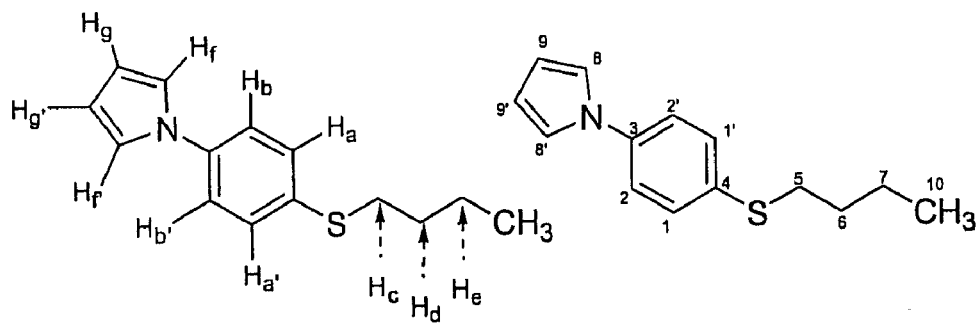

Col. 36, Line 8: "$C_2'$" should be --$C_{2'}$--

Col. 36, Line 9: "$C_3'$" should be --$C_{3'}$--

Col. 37, Line 33: "$CDC_{13}$" should be --$CDCl_3$--

Col. 38, Line 15: "$H_j$" should be --$H_i$--
Example 4g drawings should appear as follows:

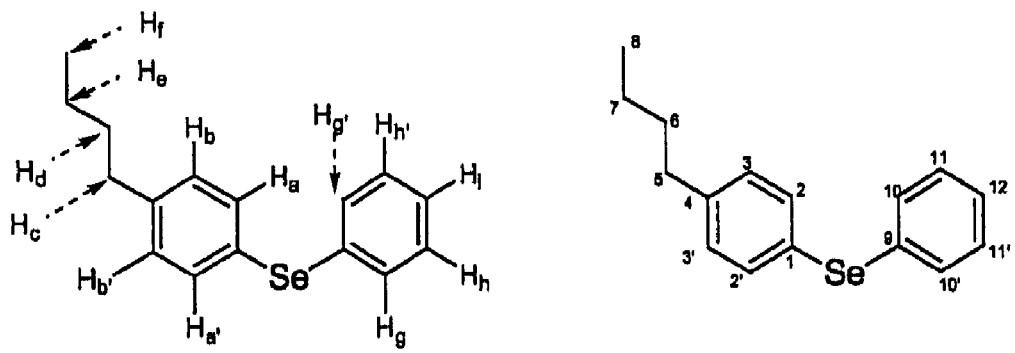

Col. 38, Line 41: "$Cl_2$" should be --$C_{12}$--

UNITED STATES PATENT AND TRADEMARK OFFICE
CERTIFICATE OF CORRECTION

PATENT NO. : 7,112,697 B1
APPLICATION NO. : 10/889311
DATED : September 26, 2006
INVENTOR(S) : Dhandapani Venkataraman et al.

It is certified that error appears in the above-identified patent and that said Letters Patent is hereby corrected as shown below:

Col. 41, Line 25: "$H_f$" should be --$H_{f'}$--
Example 4m drawings should appear as follows:

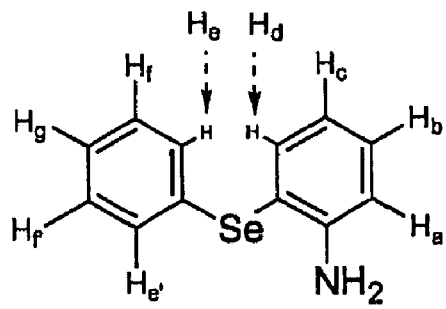
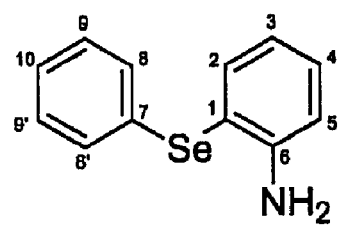

Col. 42, Line 23: "$H_f$" should be --$H_{f'}$--
Example 5b drawings should appear as follows:

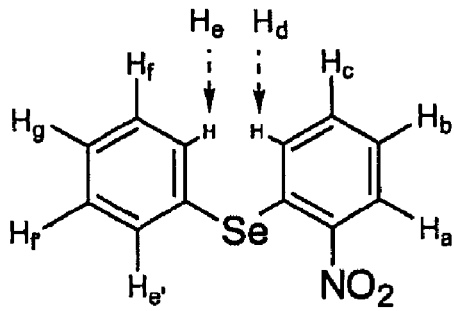
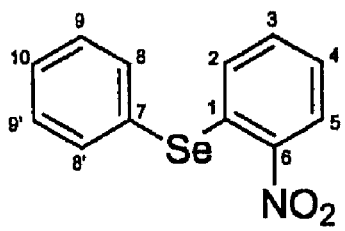

Signed and Sealed this

First Day of July, 2008

JON W. DUDAS
*Director of the United States Patent and Trademark Office*